US009551028B2

(12) United States Patent
Bjornson et al.

(10) Patent No.: US 9,551,028 B2
(45) Date of Patent: *Jan. 24, 2017

(54) NUCLEIC ACID SEQUENCE ANALYSIS

(71) Applicant: Pacific Biosciences of California, Inc., Menlo Park, CA (US)

(72) Inventors: Keith Bjornson, Fremont, CA (US); Arek Bibillo, Cupertino, CA (US); Fred Christians, Los Altos Hills, CA (US); Kevin Travers, Menlo Park, CA (US); Robin Emig, Belmont, CA (US); Stephen Turner, Seattle, WA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/552,901

(22) Filed: Nov. 25, 2014

(65) Prior Publication Data

US 2015/0167071 A1  Jun. 18, 2015

Related U.S. Application Data

(63) Continuation of application No. 13/271,889, filed on Oct. 21, 2011, now Pat. No. 8,921,046, and a continuation-in-part of application No. 12/562,690, filed on Sep. 18, 2009, now Pat. No. 8,481,264.

(60) Provisional application No. 61/392,825, filed on Oct. 13, 2010, provisional application No. 61/192,634, filed on Sep. 19, 2008.

(51) Int. Cl.
*C12Q 1/68* (2006.01)
*C07K 14/00* (2006.01)

(52) U.S. Cl.
CPC ............. *C12Q 1/6869* (2013.01); *C07K 14/00* (2013.01); *C12Q 1/6874* (2013.01)

(58) Field of Classification Search
None
See application file for complete search history.

(56) References Cited

U.S. PATENT DOCUMENTS

| | | | |
|---|---|---|---|
| 5,516,633 A | 5/1996 | Fuller | |
| 5,547,839 A | 8/1996 | Dower et al. | |
| 5,622,824 A | 4/1997 | Koster | |
| 5,648,245 A | 7/1997 | Fire et al. | |
| 5,714,320 A | 2/1998 | Kool | |
| 5,750,341 A | 5/1998 | Macevicz | |
| 5,795,782 A | 8/1998 | Church et al. | |
| 5,969,119 A | 10/1999 | Macevicz | |
| 6,210,891 B1 | 4/2001 | Nyren et al. | |
| 6,210,896 B1 | 4/2001 | Chan | |
| 6,255,083 B1 | 7/2001 | Williams | |
| 6,258,568 B1 | 7/2001 | Nyren | |
| 6,261,808 B1 | 7/2001 | Auerbach | |
| 6,306,597 B1 | 10/2001 | Macevicz | |
| 6,787,308 B2 | 9/2004 | Balasubramanian et al. | |
| 6,917,726 B2 | 7/2005 | Levene et al. | |
| 7,033,764 B2 | 4/2006 | Korlach et al. | |
| 7,052,847 B2 | 5/2006 | Korlach et al. | |
| 7,056,661 B2* | 6/2006 | Korlach ............... | C12Q 1/6869 435/287.2 |
| 7,056,676 B2 | 6/2006 | Korlach et al. | |
| 7,476,503 B2 | 1/2009 | Turner et al. | |
| 7,485,425 B2 | 2/2009 | Spier | |
| 7,901,889 B2* | 3/2011 | Christians ............ | C12Q 1/6869 435/6.12 |
| 8,153,375 B2* | 4/2012 | Travers ................ | C12Q 1/6869 435/6.1 |
| 8,481,264 B2* | 7/2013 | Bjornson ............. | C12Q 1/6874 435/6.12 |
| 8,535,882 B2* | 9/2013 | Christians ............ | C12Q 1/6869 435/6.1 |
| 8,921,046 B2* | 12/2014 | Bjornson ............. | C12Q 1/6869 435/6.12 |

(Continued)

FOREIGN PATENT DOCUMENTS

| | | |
|---|---|---|
| WO | 9106678 A1 | 5/1991 |
| WO | 9423066 A1 | 10/1994 |

(Continued)

OTHER PUBLICATIONS

Harris, TD. et al. Single-molecule DNA sequencing of a viral genome. Science, vol. 320, p. 106-109, Apr. 2008.*
Eid, et al. (2009) Real-Time DNA Sequencing from Single Polymerase Molecules, Science 323:133-138.
Friedberg, et al. (2005) Nat Rev Mol Cell Biol 6(12):943-53.
Kannouche, et al. (2004) Mol Cell 14(4):491-500.
Klungland, et al. (2007) DNA Repair (Amst) 6(4): 481-8.
Korlach, et al. (2008) Nucleosides, Nucleotides and Nucleic Acids 27:1072-1083.

(Continued)

*Primary Examiner* — Prabha Chunduru
(74) *Attorney, Agent, or Firm* — David C. Scherer; Deana A. Arnold

(57) ABSTRACT

Provided are methods for sequencing a nucleic acid with a sequencing enzyme, e.g., a polymerase or exonuclease. The sequencing enzyme can optionally be exchanged with a second sequencing enzyme, which continues the sequencing of the nucleic acid. In certain embodiments, a template is fixed to a surface through a template localizing moiety. The template localizing moiety can optionally anneal with the nucleic acid and/or associate with the sequencing enzyme. Also provided are compositions comprising a nucleic acid and a first sequencing enzyme, which can sequence the nucleic acid and optionally exchange with a second sequencing enzyme present in the composition. Compositions in which a template localizing moiety is immobilized on a surface are provided. Also provided are methods for using data from analytical reactions wherein two different enzymes are employed, e.g., at a same or different reaction regions.

21 Claims, 7 Drawing Sheets

(56) References Cited

U.S. PATENT DOCUMENTS

| | | |
|---|---|---|
| 2003/0044781 A1 | 3/2003 | Korlach et al. |
| 2003/0096253 A1 | 5/2003 | Nelson et al. |
| 2003/0190647 A1 | 10/2003 | Odera |
| 2003/0215862 A1 | 11/2003 | Parce et al. |
| 2004/0048300 A1 | 3/2004 | Sood et al. |
| 2004/0152119 A1 | 8/2004 | Sood et al. |
| 2004/0224319 A1 | 11/2004 | Sood et al. |
| 2004/0259082 A1 | 12/2004 | Williams |
| 2006/0063264 A1* | 3/2006 | Turner .................. B01L 3/5085 436/8 |
| 2008/0128627 A1 | 6/2008 | Lundquist et al. |
| 2008/0220537 A1 | 9/2008 | Foquet |
| 2009/0068655 A1 | 3/2009 | Williams |
| 2009/0131642 A1 | 5/2009 | Shenoy et al. |
| 2011/0111401 A1 | 5/2011 | Korlach et al. |
| 2011/0202280 A1 | 8/2011 | Sikora et al. |

FOREIGN PATENT DOCUMENTS

| | | |
|---|---|---|
| WO | 9627025 A1 | 9/1996 |
| WO | 9905315 A2 | 2/1999 |
| WO | 2007115205 A2 | 10/2007 |
| WO | 2011078897 A1 | 6/2011 |

OTHER PUBLICATIONS

Levene et al. (2003) "Zero Mode Waveguides for Single Molecule Analysis at High Concentrations," Science 299: 682-686.
Shamoo, et al. (1999) Cell 99(2):155-66.
Williams, JGK, et al. (2008) Nuc Ac Res 36(18):e121.
Harris, et al., "Single-Molecule DNA Sequencing of a Viral Genome," Science (2008) 320:106-109.

* cited by examiner

NUCLEIC ACID SEQUENCE ANALYSIS

CROSS-REFERENCE TO RELATED APPLICATIONS

This application is a continuation application of U.S. patent application Ser. No. 13/271,889, filed Oct. 12, 2011, which (i) claims the benefit of U.S. Provisional Application No. 61/392,825, filed Oct. 13, 2010, and (ii) is a continuation-in-part application of U.S. patent application Ser. No. 12/562,690, filed Sep. 18, 2009, now U.S. Pat. No. 8,481,264, which claims the benefit of U.S. Provisional Application No. 61/192,634, filed Sep. 19, 2008, the disclosures of all of which are incorporated herein by reference in their entireties for all purposes.

BACKGROUND OF THE INVENTION

Nucleic acid sequence data is valuable in myriad applications in biological research and molecular medicine, including determining the hereditary factors in disease, in developing new methods to detect disease and guide therapy (van de Vijver et al. (2002) "A gene-expression signature as a predictor of survival in breast cancer," New England Journal of Medicine 347: 1999-2009), and in providing a rational basis for personalized medicine. Obtaining and verifying sequence data for use in such analyses has made it necessary for sequencing technologies to undergo advancements to expand throughput, lower reagent and labor costs, and improve accuracy (See, e.g., Chan, et al. (2005) "Advances in Sequencing Technology" (Review) Mutation Research 573: 13-40, and Levene et al. (2003) "Zero Mode Waveguides for Single Molecule Analysis at High Concentrations," Science 299: 682-686), the disclosures of which are incorporated herein in their entireties for all purposes.

Single molecule real-time sequencing (SMRT) is a highly parallel sequencing-by-synthesis technology that permits the simultaneous surveillance of, e.g., thousands of sequencing reactions in arrays of multiplexed detection volumes, e.g., zero-mode waveguides (ZMWs). (See e.g., Levene et al. (2003) Zero-mode waveguides for single-molecule analysis at high concentrations, Science 299:682-686; Eid, et al. (2009) Real-Time DNA Sequencing from Single Polymerase Molecules, Science 323:133-138; U.S. Ser. No. 12/767,673, filed Apr. 26, 2010; Published U.S. Patent Application Nos. 2010/0221716 and 2003/0044781; and U.S. Pat. Nos. 6,917,726 and 7,056,661, the disclosures of which are incorporated herein in their entireties for all purposes). Each detection volume in an array creates an illuminated visualization chamber that is small enough to observe the template-dependent synthesis of a single single-stranded DNA molecule by a single DNA polymerase.

When a particular base in the template strand is encountered by the polymerase during the polymerization reaction, e.g., in a ZMW, the enzyme complexes with an available fluorescently labeled nucleotide or nucleotide analog and incorporates that nucleotide or nucleotide analog into the nascent growing nucleic acid strand. During this time, the fluorophore emits fluorescent light whose color corresponds to the nucleotide's or analog's base identity. The polymerase cleaves the bond linking the fluorophore to the nucleotide or analog during the nucleotide incorporation cycle, permitting the dye to diffuse out of the detection volume. The signal returns to baseline, and the process repeats.

A single molecule sequencing reaction is typically localized to a detection volume by immobilizing a DNA polymerase enzyme within or proximal to the site at which the reaction takes place. Ideally, the immobilized polymerase retains its activity and can be used repeatedly and continuously in multiple sequencing reactions. However, it has been observed that in some cases, the processivity, accuracy, and/or activity of the polymerase enzyme can decrease. In particular, in at least some cases, damage to the DNA polymerase, e.g., by exposure to optical energy during fluorescent or chemiluminescent detection, can have a detrimental effect on the enzyme's activity.

Current strategies for single molecule sequencing-by-synthesis employ a polymerase that has been tethered within or proximal to a reaction region within a detection volume, e.g., in a ZMW. What is needed in the art are new methods and compositions that can maintain the processivity, accuracy, and polymerase activity in, e.g., a single-molecule sequencing reaction, while still localizing the polymerization reaction to a defined observation volume. The invention described herein fulfills these and other needs, as will be apparent upon review of the following.

SUMMARY OF THE INVENTION

In certain aspects, the present invention provides methods and related compositions useful for immobilizing a template nucleic acid (or "nucleic acid template") at a reaction region. The compositions include a template localizing moiety that is covalently attached to a surface, e.g., a single molecule reaction region. The moiety can associate with a template nucleic acid, e.g., a DNA, RNA, or analogs or derivatives thereof, present in the composition and fix the template to the surface, e.g., localizing the nucleic acid to the surface. A sequencing enzyme, e.g., a polymerase, reverse transcriptase, exonuclease, etc., can optionally associate with the template localizing moiety and perform template-directed sequencing of the template nucleic acid. In preferred embodiments, the sequencing enzyme can exchange with other sequencing enzymes present in the composition without disrupting or terminating sequencing of the template, thus permitting, e.g., a photodamaged sequencing enzyme to exchange with a non-photodamaged sequencing enzyme. Immobilizing a nucleic acid template via a template localizing moiety can advantageously allow longer uninterrupted sequence reads in, e.g., synthesis- or degradation-based single-molecule sequencing reactions. In certain aspects, the present invention provides methods and related compositions useful for performing template-directed synthesis of a nucleic acid. In certain aspects, the invention provides methods and related compositions for performing exonuclease sequencing of a nucleic acid. While various embodiments are described herein in terms of enzymatic reactions, and more particularly nucleic acid sequencing reactions, it will be clear to one of ordinary skill that the methods are also applicable to other types of analytical reactions, e.g., binding assays, antibody assays, complex formation analysis, kinetic studies, and the like; and are especially desirable in analytical reactions that are condition dependent such that they can be repeatedly performed under different reaction conditions.

In a first aspect, the invention provides methods of performing template-directed synthesis of a nucleic acid that include fixing a template nucleic acid to a solid surface through a template localizing moiety, e.g., that topologically encircles the template. The template localizing moiety can be a polymer, including but not limited to a polypeptide (e.g., other than a polymerase to be used in the template-directed synthesis reaction), polynucleotide, synthetic polymer, and combinations thereof. The methods include synthesizing a nascent strand from at least a portion of the template nucleic acid with a first polymerase, exchanging the first polymerase with a second polymerase, and continuing synthesis of the nascent strand with the second polymerase. Optionally, exchanging the first polymerase can include exchanging a photodamaged polymerase with a polymerase that is not photodamaged, and synthesis can optionally be continued with the second, non-photodamaged polymerase. Such embodiments can further comprise a template nucleic acid that is circular. In certain preferred embodiments the template nucleic acid is subjected to the template-directed synthesis reaction multiple times with one or more polymerases to generate a single nucleic acid strand comprising multiple copies of a polynucleotide complementary to the template nucleic acid.

In a further aspect, the invention provides methods of performing exonuclease sequencing of a nucleic acid that include fixing a template nucleic acid to a solid surface through a template localizing moiety, e.g. a polypeptide other than a polymerase or other polymer that topologically encircles the template. The methods include degrading a first strand of the template nucleic acid with a first exonuclease and detecting the nucleotides so released, exchanging the first exonuclease with a second exonuclease, and continuing degradative sequencing of the first strand with the second exonuclease. Optionally, exchanging the first exonuclease can include exchanging a photodamaged exonuclease with an exonuclease that is not photodamaged, and degradation can optionally be continued with the second, non-photodamaged exonuclease.

In a related aspect, the invention provides compositions that can be used in the methods described above. The compositions include a template nucleic acid tethered to a solid surface through a template localizing moiety, e.g., a moiety that topologically encircles the template, and a first sequencing enzyme capable of sequencing the template nucleic acid. The template localizing moiety can comprise a polymer (natural or synthetic), e.g., a polypeptide, polynucleotide, synthetic polymer, and analogs, derivatives, mimetics, and combinations thereof. In certain specific embodiments, the template localizing moiety comprises a protein, e.g., a hexameric helicase, a PCNA, a T4 phage gp45 protein, or a β subunit of a eubacterial DNA polymerase. In other specific embodiments, the template localizing moiety comprises a polynucleotide comprising a nucleotide sequence complementary to a portion of the template nucleic acid, and the first sequencing enzyme is a polymerase capable of strand displacement of the polynucleotide from the template nucleic acid. In certain embodiments, the first sequencing enzyme is a first polymerase, e.g., capable of synthesizing a nascent strand based on the nucleotide sequence of the template nucleic acid, and the template localizing moiety permits the first polymerase to be exchanged with a second polymerase present in the composition without terminating template-directed synthesis, e.g., the second polymerase is capable of continuing the sequencing of the template nucleic acid. The polymerase can optionally be, e.g., a DNA or RNA polymerase, e.g., a Klenow fragment, Φ29, AMV, B103, GA-1, HIV-1 PZA, Φ15, BS32, M-MLV, M2Y, Nf, G1, Cp-1, PRD1, PZE, SF5, Cp-5, Cp-7, PR4, PR5, PR722, L17, T4, an Archeal, an Eukaryal, or an Eubacterial polymerase, or mutations or modified versions thereof. Optionally, the template nucleic acid may be single-stranded or circular, and in some preferred embodiments is both single-stranded and circular. Optionally, the polymerase present in the compositions can be non-covalently attached to the template localizing moiety.

The compositions can optionally include ATP, CTP, GTP, TTP, UTP or ITP, which can modulate the rate of polymerization in a concentration-dependent manner, e.g., when the template localizing moiety and the polymerase participate in a template-dependent polymerization reaction. The compositions can optionally include one or more fluorescently labeled nucleotides or nucleotide analogs that can photodamage the polymerase. In some embodiments, the template localizing moiety is not susceptible to photo-induced damage caused by the one or more fluorescently labeled nucleotide or nucleotide analogs.

Compositions that include a template localizing moiety immobilized on a planar surface, in a well, or in a single molecule reaction region, e.g., a zero-mode waveguide are also provided by the invention. The immobilized moiety can optionally comprise, e.g., a polymer (e.g., natural or synthetic) including but not limited to a polynucleotide and/or a polypeptide, e.g., a protein other than a polymerase, such as a processive nuclease, a single-strand binding protein (SSBP), a helicase, a DNA repair enzyme, a DNA processivity factor, or a protein that non-specifically binds a double-stranded nucleic acid. The template localizing moiety can optionally topologically encircle a template DNA strand when a DNA strand is present in the composition. The template localizing moiety that topologically encircles the template can optionally comprise a PCNA, a T4 phage gp45 protein, a β subunit of a eubacterial polymerase, one or more synthetic structural units, and/or a polynucleotide, where the polynucleotide optionally comprises a portion that is complementary to at least a portion of the template nucleic acid. In certain preferred embodiments, the template localizing moiety that topologically encircles the template comprises at least one polynucleotide portion and at least one portion comprising synthetic structural units, e.g., at least some of which are polyethylene glycol units. The compositions can optionally include a template DNA, e.g., a single-stranded DNA and/or a closed loop of DNA, which the template localizing moiety can associate with and/or retain, and fix to the planar surface, in a well, or in a single molecule reaction region, e.g., comprising a zero-mode waveguide.

Compositions in which a template localizing moiety is immobilized to a planar surface, well, or single-molecule reaction region can optionally include a sequencing enzyme, e.g., an exonuclease (e.g., T7 exonuclease, lambda exonuclease, mung bean exonuclease, ExoI, Exo III, Exo IV, ExoVII, exonuclease of Klenow fragment, exonuclease of PolI, Taq exonuclease, T4 exonuclease, etc.) or DNA polymerase (e.g., a Klenow fragment, Φ29, B103, GA-1, PZA, Φ15, BS32, M2Y, Nf, G1, Cp-1, PRD1, PZE, SF5, Cp-5, Cp-7, PR4, PR5, PR722, or L17 polymerase.) Optionally, the sequencing enzyme can be non-covalently attached to the moiety, or it can be covalently attached to the moiety, e.g., via a DNA polymerase's C-terminal end. The template localizing moiety can optionally improve the accuracy and/or processivity of the sequencing enzyme, when the moiety and the sequencing enzyme participate in a nucleic acid sequencing reaction, e.g., a sequencing-by-synthesis reaction or degradation-based sequencing reaction. These compositions can optionally include ATP, CTP, GTP, TTP, UTP or ITP, and/or one or more fluorescently labeled nucleotides or nucleotide analogs, as described above.

In certain embodiments, the invention provides sequencing reactions that include a nucleic acid template, a synthesis initiating moiety that complexes with or is integral to the template, a DNA polymerase, and a template localizing moiety immobilized on a substrate, e.g., a planar surface, well, or single molecule reaction region, e.g., a zero mode waveguide. The DNA polymerase of the sequencing reaction can optionally associate with the immobilized template localizing moiety. The polymerase and the template localizing moiety can optionally be non-covalently attached. Optionally, the DNA polymerase can be covalently attached to the moiety, e.g., via the polymerase's C-terminal end.

In certain embodiments, the invention provides sequencing reactions that include a nucleic acid template, a synthesis initiating moiety that complexes with or is integral to the template, a DNA polymerase, a template localizing moiety immobilized on a substrate, which can comprise a planar surface, a well, and/or a single molecule region, e.g., a zero-mode waveguide. In certain embodiment, the sequencing reactions provided herein further comprise a luciferase-based detection system for monitoring pyrophosphate release. The DNA polymerase or components of the luciferase-based detection system (e.g., luciferase, sulfurylase, etc.) can optionally associate (covalently or non-covalently) with the immobilized template localizing moiety.

The sequencing reactions provided by the invention can optionally include one or more fluorescently labeled nucleotides or nucleotide analogs. A polymerase present in the sequencing reaction can optionally synthesize a complementary nascent strand from at least a portion of the template in a template-dependent matter, optionally incorporating one or more fluorescently labeled nucleotides or nucleotide analog into the resulting nascent strand. In certain embodiments, the sequencing reaction comprises a pool of nucleic acid templates, and optionally, the template localizing moiety (or plurality thereof) comprises a polynucleotide complementary to only one or a subset of the nucleic acid templates in the pool. The polymerase can be non-covalently or covalently attached to the template localizing moiety, e.g., at a C-terminal portion of the polymerase.

In a related aspect, the invention provides sequencing systems that include a reaction region, e.g., a planar surface, one or more well, or one or more single molecule reaction region, and a template localizing moiety immobilized within or proximal to the reaction region. Optionally, the single-molecule reaction region included in the systems can be a zero-mode waveguide. Optionally, the systems can include a sequencing enzyme (e.g., a polymerase or nuclease) in the reaction region. The template localizing moiety in the systems can optionally be configured to interact with a sequencing enzyme, when a sequencing enzyme is present in the reaction region. The sequencing enzyme and the template localizing moiety can optionally be covalently attached or non-covalently attached, as described above.

The systems of the invention also include a detector configured to detect a sequencing product formed in the reaction region. A sequencing product of the invention includes but is not limited to a newly synthesized nucleic acid strand ("nascent strand"), released pyrophosphate, and nucleotides released by exonuclease degradation. The detector can optionally be configured to detect fluorescent light from one or more fluorophores that is, e.g., linked to a nucleotide or nucleotide analog. The system can optionally comprise an epifluorescent detector.

In a further aspect, the invention provides a method of sequencing a template nucleic acid that includes fixing a circular template to a solid surface through a template localizing moiety, annealing an oligonucleotide primer to the template nucleic acid, initiating template-directed nascent strand synthesis by a polymerase that is not immobilized to the solid surface, and detecting incorporations of nucleotides into the nascent strand. A temporal sequence of the incorporations is indicative of the sequence of the nucleic acid. Optionally, the incorporations are detected by monitoring signals from detectable labels linked to the nucleotides as they are being incorporated into the nascent strand, e.g., where the type of detectable label corresponds to the base composition of a nucleotide. Preferably, the detectable labels are removed during incorporation resulting in a nascent strand that does not comprise the detectable labels. More preferably, the detectable labels are removed during incorporation resulting in a nascent strand that does not comprise the detectable labels or any other element (e.g., linker or fragment thereof) used to link the detectable labels to the nucleotides, e.g., to provide an entirely "natural" nascent strand. Optionally, the incorporations are detected using a luciferase-mediated detection system. In certain preferred embodiments, the template localizing moiety topologically encircles the template nucleic acid. In some embodiments, the template nucleic acid is a single-stranded nucleic acid molecule. The sequencing methods can further comprise sequencing the template nucleic acid multiple times to generate a single nascent strand comprising multiple copies of a polynucleotide complementary to the template nucleic acid. Further, in some embodiments the polymerase is a plurality of polymerase enzymes, wherein only a single polymerase enzyme is engaged in template-directed nascent strand synthesis on a single template at a given time.

In a further aspect, methods for generating redundant sequence information from a single template nucleic acid molecule using multiple sequencing enzymes are provided. In certain embodiments, such a method comprises attaching a single template nucleic acid molecule to a solid surface; sequencing a polynucleotide region of the single template nucleic acid molecule with a first sequencing enzyme to obtain a first polynucleotide sequence read of the polynucleotide region; exchanging the first sequencing enzyme with a second sequencing enzyme; and sequencing the polynucleotide region of the single template nucleic acid molecule with the second sequencing enzyme to obtain a second polynucleotide sequence read of the polynucleotide region, wherein the first and second polynucleotide sequence reads comprise redundant sequence information for the polynucleotide region, thereby generating redundant sequence information from a single template nucleic acid molecule. It will be understood that by "first sequencing enzyme" in this method, it is meant that a single (i.e., one) sequencing enzyme (as opposed to multiple polymerases of the same type) is used to generate the entire first polynucleotide sequence read; likewise, the "second sequencing enzyme" is a single (i.e., one) sequencing enzyme used to generate the second polynucleotide sequence read. This is different from "flush-and-scan" methods in which there are buffer exchanges that replace polymerases during sequencing such that multiple polymerases must participate to generate a single polynucleotide read for a single polynucleotide region. The first and second sequence reads necessarily overlap to generate the redundant sequence information, so the same polynucleotide region of the template nucleic acid molecule is sequenced by both the first and second sequencing enzymes. Both the first polynucleotide sequence read and the second polynucleotide sequence read are optionally subjected to statistical analysis to determine a consensus polynucleotide sequence of the polynucleotide region of the single template nucleic acid molecule. In certain embodiments, the single template nucleic acid molecule is attached to the solid surface through a template localizing moiety. In some embodiments, the sequencing enzymes are polymerase enzymes, e.g., having different characteristics, e.g., fidelity, processivity, accuracy, activity, specificity, rate, retention time, sequence context sensitivity, and stability. The methods optionally comprise sequencing the polynucleotide region of the single template nucleic acid molecule multiple times with at least one of the first or second sequencing enzyme, and such resequencing of a single template by a single polymerase also generates redundant sequence information. In certain embodiments, the template nucleic acid molecule is a circular template nucleic acid molecule, the first sequencing enzyme is a first type of polymerase enzyme, and the second sequencing enzyme is a second type of polymerase enzyme. For example, such an embodiment can comprise sequencing the polynucleotide region of the single template nucleic acid molecule more than two times using both the first and second polymerase enzymes to generate a single nucleic acid strand comprising multiple copies of a polynucleotide complementary to the polynucleotide region. The first and second sequencing enzymes can be present in the same reaction mixture, or in different reaction mixtures, e.g., that are separately introduced to the single template nucleic acid molecule. The methods can further include recording the first polynucleotide sequence read and the second polynucleotide sequence read on computer-readable media. Yet further, the sequencing by the first sequencing enzyme can be performed under a first set of reaction conditions, and the sequencing by the second sequencing enzyme can be performed under a second set of reaction conditions different from the first set of reaction conditions. Reaction conditions can differ from one another by at least one aspect selected from the group consisting of temperature, pH, types of nucleotides, types of labels, types of buffer, ion concentrations, illumination, and types of divalent or monovalent cations.

In another aspect, methods for performing analytical reactions are provided. Such methods typically comprise providing first and second reaction condition; carrying out analytical reactions under the first and second reaction condition, either simultaneously or sequentially; obtaining first and second sets of reaction data from the analytical reaction under the first and second reaction conditions, respectively; and analyzing the first set of reaction data and the set of second reaction data in combination to determine a final set of reaction data that is more reflective of the analytical reaction than either the first set of reaction data or the set of second reaction data alone. The first and second reaction conditions can be provided at a single reaction region, or a different reaction regions, e.g., in an array. In certain embodiments, the first reaction condition comprises a first enzyme and the second reaction condition comprises a second enzyme, and the first and second enzymes have different characteristics during the analytical reaction. For example, the first enzyme and second enzyme can have different error profiles, e.g., complementary error profiles. The first and second enzyme can optionally be localized in different reaction regions. In some embodiments, the first reaction condition comprises a first template nucleic acid and the second reaction condition comprises a second template nucleic acid, wherein the first and second template nucleic acids comprise different nucleotide sequences, which can optionally comprise complementary nucleotide sequences. The first template nucleic acid and second template nucleic acid are optionally localized in different reaction regions, e.g., via an interaction with a template localizing moiety at a reaction region. In yet further embodiments, the first reaction condition and the second reaction conditions differ in at least one of the group consisting of temperature, pH, divalent cation concentration, illumination, buffer, and labeling groups present. In certain embodiments, at least one of the analytical reactions is carried out iteratively to generate redundant reaction data in a single analytical reaction. In certain embodiments, the analytical reaction is an enzymatic reaction. In specific embodiments, the analytical reaction is a nucleic acid sequencing reaction, and, optionally, the final set of reaction data comprises a consensus nucleotide sequence. In other embodiments, the analytical reaction is a binding assay, a kinetic assay, a complex formation assay, or an antibody assay that exhibits different behavior, and therefore altered reaction data, under the different reaction conditions.

In some aspects, reaction mixtures are provided comprising a single template nucleic acid molecule attached to a solid surface in a single molecule reaction region; a first type of polymerase; a second type of polymerase; a set of different nucleotide analogs of the invention, at least one nucleotide analog of which comprises a detectable moiety linked to a phosphate moiety that is released upon incorporation of said one nucleotide analog into a complementary copy of the single template nucleic acid molecule; and multiple polynucleotide complements of the single template nucleic acid molecule, wherein some of the polynucleotide complements were synthesized by a single one of the first type of sequencing enzyme and others of the polynucleotide complements were synthesized by a single one of the second type of sequencing enzyme. In certain embodiments, the template nucleic acid is attached to the solid support through a template localizing moiety. Optionally, the polymerases are selected from the group consisting of a Klenow fragment, Φ29, B103, GA-1, AZA, Φ15, BS32, M-MLV, M2Y, Nf, G1, Cp-1, PRD1, PZE, SF5, Cp-5, Cp-7, PR4, PR5, PR722, and L17 polymerase. In preferred embodiments, the first type of polymerase has at least one characteristic that differs from the second type of polymerase, and some examples of characteristics that can differ between polymerases include, but are not limited to, fidelity, processivity, accuracy, activity, specificity, rate, retention time, sequence context sensitivity, and stability. The template nucleic acid can be single-stranded or double-stranded, and is typically circular. The multiple polynucleotide complements are preferably within a linear concatemer molecule. In certain preferred embodiments, the detectable moiety is a fluorescent label. In certain preferred embodiments, the single molecule reaction region is within a zero-mode waveguide.

In yet further aspects, methods are provided for sequencing a single template nucleic acid molecule. Such methods typically comprise attaching the single template nucleic acid molecule to a solid surface; annealing an oligonucleotide primer to the template nucleic acid; using a first single polymerase to perform template-directed nascent strand synthesis using a polynucleotide region of the single template nucleic acid molecule to generate a first polynucleotide complement of the polynucleotide region, where the first single polymerase is a first type of polymerase that is not immobilized to the solid surface; detecting a first set of incorporations to generate a first temporal sequence of incorporations into the first polynucleotide complement, the first temporal sequence of incorporations comprising each nucleotide base incorporated during the template-directed nascent strand synthesis of step c; using a second single polymerase to perform template-directed nascent strand synthesis using the polynucleotide region of the single template nucleic acid molecule to generate a second polynucleotide complement of the polynucleotide region, where the second single polymerase is a second type of polymerase that is not immobilized to the solid surface; detecting a second set of incorporations to generate a second temporal sequence of incorporations into the second polynucleotide complement, the second temporal sequence of incorporations comprising each nucleotide base incorporated during the template-directed nascent strand synthesis of step e; and analyzing the first temporal sequence and the second temporal sequence to determine a consensus sequence for the polynucleotide region of the single template nucleic acid molecule. In some embodiments, the template nucleic acid is a circular nucleic acid and/or a single-stranded nucleic acid, and optionally is attached to the solid surface through a template localizing moiety. In some embodiments, nucleotides used in the template-directed nascent strand synthesis comprise detectable labels that identify the base composition of the nucleotides. The first and second types of polymerases can be present together in the same reaction mixture, or in different reaction mixtures, e.g., that are separately introduced or exposed to the single template nucleic acid molecule. The different reaction mixtures may have other differences besides polymerase composition, including but not limited to, temperature, pH, types of nucleotides, types of labels, types of buffer, ion concentrations, type of illumination, and types of divalent or monovalent cations.

In yet further aspects, devices are provided that comprise a solid surface comprising single molecule reaction regions having template nucleic acids immobilized therein, where each of the single molecule reaction regions has no more than one of the template nucleic acids immobilized therein; and a reaction mixture comprising multiple types of polymerase enzymes capable of performing template-dependent nascent strand synthesis on the individual template nucleic acids. In certain embodiments, such a device comprises template nucleic acids localized in the single molecule reaction regions through a template localizing moiety. The single molecule reaction regions are optionally within optical confinements, e.g., zero-mode waveguides. Further, in some embodiments, the multiple types of polymerase enzymes are simultaneously carrying out template-directed synthesis at different single molecule reaction regions on the solid surface.

In yet further aspects, methods for sequencing a plurality of identical template nucleic acids are provided. In certain embodiments, such methods comprise attaching single molecules of the identical template nucleic acids to different single molecule reaction regions on a solid surface; exposing the solid surface to a reaction mixture comprising at least two different types of polymerases; forming a plurality of complexes at the single molecule reaction regions, the complexes comprising a single one of the molecules of the identical template nucleic acids and a single polymerase selected from the at least two different types of polymerases; within each complex, using the single polymerase to synthesize a polynucleotide strand complementary to the single molecule of template nucleic acid; detecting a set of incorporations of nucleotides into the polynucleotide strand synthesized in each of the complexes, thereby generating a plurality of sequence reads for the identical template nucleic acids, wherein some of the sequence reads were generated by a first of the different types of polymerases and others of the sequence reads were generated by a second of the different types of polymerases; and subjecting the plurality of sequence reads to statistical analysis to determine a consensus sequence for the identical template nucleic acids. Optionally, the identical template nucleic acids can be attached to the single molecule reaction regions through template localizing moieties. Preferably, nucleotides used to synthesize the polynucleotide strand comprise detectable labels that identify the base composition of the nucleotides. In certain embodiments, the first of the different types of polymerases has at least one characteristic that differs from the second of the different types of polymerases, and this characteristic can be, e.g., related to polymerase fidelity, processivity, accuracy, activity, specificity, rate, retention time, sensitivity to sequence context, and stability, e.g., under a given set of reaction conditions. In certain embodiments, the methods further comprise repeating the template-directed nascent strand synthesis under at least two reaction conditions that differ from each other in at least one aspect, including but not limited to, temperature, pH, types of nucleotides, types of labels, types of buffer, ion concentrations, and types of divalent or monovalent cations.

Those of skill in the art will appreciate that the methods provided by the invention for sequencing of a nucleic acid, e.g., a DNA, can be used alone or in combination with any of the compositions described herein. DNA sequencing systems that include any of the compositions described herein are also a feature of the invention. Such systems can optionally include detectors, array readers, excitation light sources, and the like.

The present invention also provides kits that incorporate the compositions of the invention. Such kits can include, e.g., a template localizing moiety packaged in a fashion to permit its covalent binding to a surface of interest. Alternatively, the surface bound template localizing moieties can be provided as components of the kits, or the surface can be provided with binding partners suitable to bind the template localizing moieties, which are optionally packaged separately. Instructions for making or using surface bound template localizing moieties are an optional feature of the invention.

Such kits can also optionally include additional useful reagents such as one or more nucleotide analogs, e.g., for sequencing, nucleic acid amplification, or the like. For example, the kits can include a DNA polymerase packaged in such a manner as to enable its use with the template localizing moiety, a set of different nucleotide analogs of the invention, e.g., those that are analogous to A, T, G, and C, e.g., where one or more of the analogs comprise a detectable moiety, to permit identification in the presence of the analogs. The kits of the invention can optionally include natural nucleotides, a control template, and other reagents, such as buffer solutions and/or salt solutions, including, e.g., divalent metal ions, e.g., $Mg^{++}$, $Mn^{++}$ and/or $Fe^{++}$, standard solutions, e.g., dye standards for detector calibration, etc. Such kits can optionally include various sequencing enzymes (e.g., one or more polymerases or nucleases), and components required for detection of a sequencing product, e.g., luciferase-based detection system. Such kits also typically include instructions for use of the compounds and other reagents in accordance with the desired application methods, e.g., nucleic acid sequencing, nucleic acid labeling, amplification and the like.

DETAILED DESCRIPTION

Overview

Figure 1:
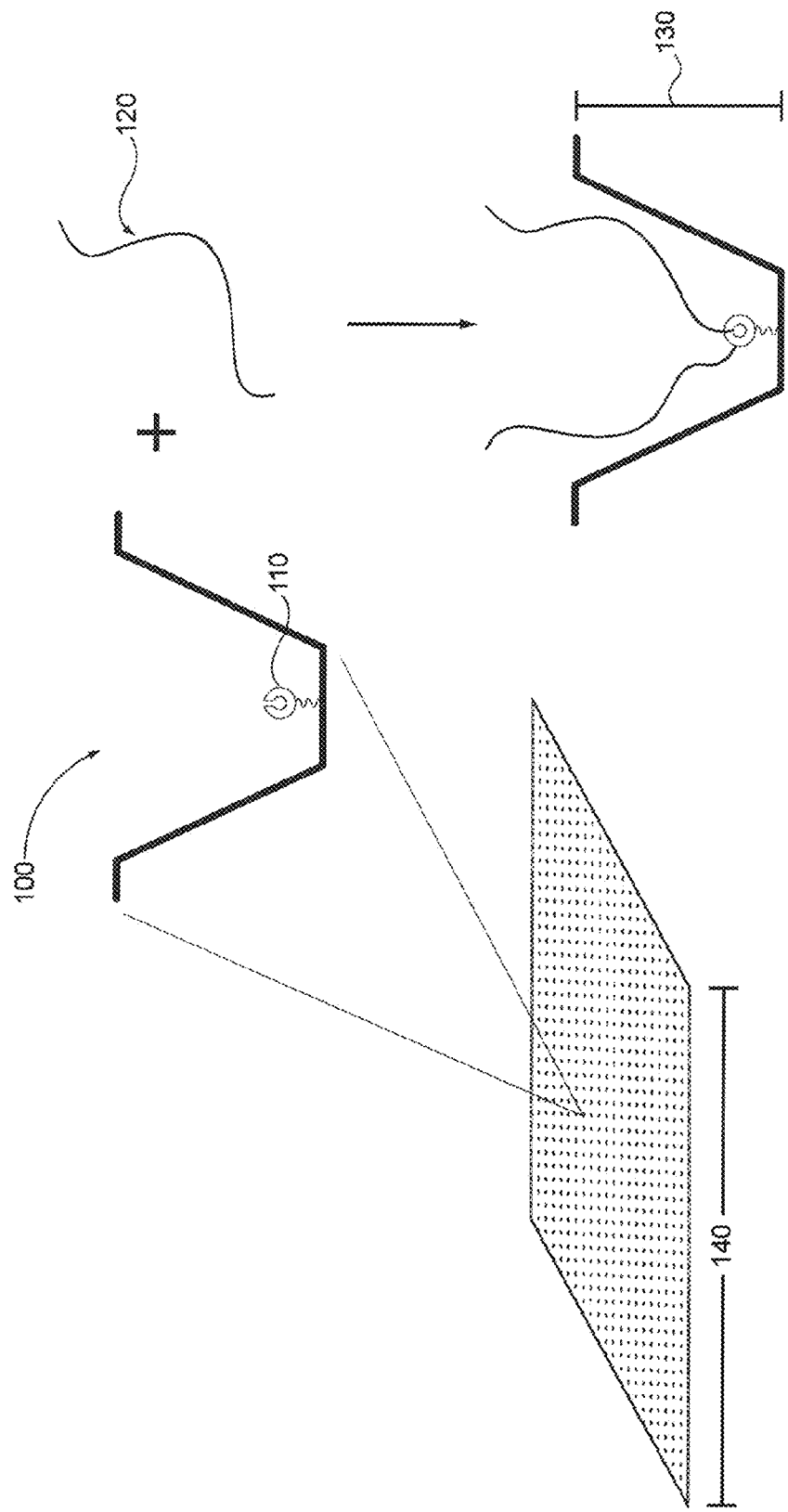
FIG. 1 provides a schematic depiction of a surface-immobilized template localizing moiety fixing a template nucleic acid to the surface by topologically encircling the template.

Analysis of small reaction volumes, e.g., for single-molecule reactions, is becoming increasingly important in high throughput applications, e.g., in nucleic acid sequencing, antibody studies, analysis of the kinetics of single molecules and molecular complexes, binding assays, drug screening assays, the association of components of single molecular complexes, and the like. Often the results of these analytical studies are influenced by various characteristics of the reaction conditions under which the studies are performed. Such reaction condition characteristics include temperature, pH, buffer, divalent cation composition, temperature, pH, and the particular reaction components that are interacting within the reaction, e.g., reactive proteins, enzyme, cofactors, substrates, binding agents/partners, etc. For example, the presence of a particular type of a given class of enzyme, substrate, cofactor, etc. as opposed to a different type of enzyme, substrate, cofactor, etc. is considered to be a characteristic of a reaction condition, and changing such a characteristic is considered changing the reaction condition. Changing the reaction conditions for an analytical reaction can influence the reaction data, both directly and indirectly, e.g., by affecting the attributes and/or activities of the reaction components involved in the analytical reaction. The differing impacts of various characteristics of reaction conditions on an analytical reaction have traditionally confounded analysis of the reaction, e.g., by introducing bias, errors, and other inconsistencies that were difficult to identify during reaction data analysis. In certain aspects, the present invention instead takes advantage of these previously confounding reaction condition-based effects to provide higher quality reaction data by performing an analytical reaction under different conditions, and using the data from these reactions together to analyze the analytical reaction. As such, the invention provides experimental systems in which an analytical reaction performed under a first reaction condition provides a first data set, and the analytical reaction performed under a second reaction condition provides a second data set. The first and second data sets are used together to determine a final data set that best represents the analytical reaction. In particular embodiments, inconsistencies between the first data set and the second data set are resolved by determining which reaction condition (e.g., the first reaction condition) provides the best environment for accurate data at that point in the analytical reaction. For example, it may be determined that data from the first data set is more reliable at a first time point, and data from the second data set is more reliable at a second time point. Therefore, the data from the first data set (and not the second data set) is selected for inclusion in the final data set for the first time point, and the data from the second data set (and not the first data set) is selected for inclusion in the final data set for the second time point. The final data set thus comprises a combination of data from both the first and second data sets. In this way, condition-based bias in an experimental system can be selectively "cancelled out" by using different reaction conditions having different condition-based biases and the quality of the final data set is improved.

An analytical reaction can be repeated on a single molecule or molecular complex, e.g., as when a single template molecule is repeatedly subjected to template-dependent nascent strand synthesis, or when a single immobilized binding agent is repeatedly exposed to a non-immobilized binding partner. Alternatively or in addition, an analytical reaction can be repeated by simultaneously or sequentially performing it on multiple, different molecules or molecular complexes under the same or different reaction conditions. Further, such methods typically involve immobilization of at least one component of the reaction, e.g., an enzyme or substrate for the enzyme, a binding agent, etc. For example, a template nucleic acid can be immobilized and multiple different polymerases used to sequence the template, thereby providing multiple different sequencing reaction conditions at a single reaction site. Alternatively, multiple different types of polymerases can be immobilized, e.g., at known or determinable locations on a substrate, and used to sequence the same template once or multiple times (e.g., using circular template molecules or templates localized at the reaction site to allow rebinding and resequencing by the same polymerase), thereby providing multiple different sequencing reaction conditions at multiple different reaction sites. In further embodiments, multiple different types of polymerases are used with a template preparation that comprises a plurality of fragments of a nucleic acid sample of interest, e.g., an amplified nucleic acid sample. For example, a genomic DNA or RNA sample can be amplified, e.g., by whole genome amplification or random amplification methods, and the resulting amplicons sequenced in a reaction mixture comprising a plurality of immobilized, optically resolvable polymerase enzymes, where the plurality optionally comprises different types of polymerase enzymes. In such embodiments, the template preparation does not necessarily comprise identical template molecules, especially when fragmentation or amplification is randomized. However, a particular nucleotide sequence or region of interest is expected to be present multiple times, e.g., in amplicons or fragments of different sizes. As such, reference herein to identical templates refers not only to identical template molecules but also to segments of templates that comprise the same sequence or region of interest, even if the molecules are not wholly identical.

As noted above, different characteristics possessed by different types of a given class of reaction components, e.g., in a single-molecule reaction, can affect the data collected from such a reaction. For example, different types of a particular class of enzymes (e.g., polymerases, nucleases, ligases, etc.) have different activities, specificities, sensitivities, rates, error profiles, etc. that distinguish them from one another and also affect how they function in an analytical reaction. As a result, data from a given reaction can be affected or influenced by exchanging one type of reaction component in a class for a second type of reaction component in the same class, e.g., exchanging different types of polymerases to sequence and resequence a single template nucleic acid, or using different types of polymerases in a plurality of independent single molecule sequencing reactions, each having a different copy of the same template nucleic acid. Likewise, different binding agents that bind the same binding partner (e.g., different types of receptors for the same ligand) can have different affinities, rates of association and/or dissociation, stabilities, etc. Optionally, a plurality of reaction condition characteristics can be changed in combination to provide a set of varying reaction conditions in which to carry out an analytical reaction of interest.

An understanding of the characteristics of the reaction components under the set of reaction conditions used is highly beneficial during analysis of the data from the analytical reaction(s). For example, when two polymerases with complementary characteristics are used to repeatedly sequence a single template (e.g., a single template molecule or a set of template molecules comprising overlapping or identical nucleotide sequences), the sequence reads generated by the first polymerase can be analyzed based on its known characteristics, the sequence reads generated by the second polymerase can be analyzed based on its known characteristics, and the sequence reads can be used together to construct a consensus sequence for the template, where each nucleotide position is determined based on data from both the first and second polymerase as well as their known characteristics. In some embodiments, the determination of the final consensus sequence can be carried out by combining all the individual reads together in a single operation, and in other embodiments multistep operations are used, e.g., wherein the reads from the first polymerase are used to generate a first consensus sequence, the reads from the second polymerase are used to generate a second consensus sequence, and the first and second consensus sequences are analyzed together to determine a final consensus sequence. Further, although the present example uses reaction conditions that differ in the type of polymerase therein, other changes in reaction conditions (e.g., changes in single characteristics such as temperature, pH, divalent cation, etc., or combinations thereof) can also be used as a basis for dividing up the data and determining a set of consensus sequences to be used to derive a final consensus sequence. For example, data from reactions performed at a first pH can be used to derive a first consensus sequence and data from reactions performed at a second pH can be used to derive a second consensus sequence. In another example, the data are divided up based on multiple different reaction characteristics (e.g., pH and enzyme type) to provide a consensus sequence for each reaction condition (e.g., enzyme 1, pH1; enzyme 2, pH2; enzyme 1, pH2; and enzyme 2, pH1), which are subsequently analyzed to determine a final consensus sequence.

Yet further, different enzyme substrates can also introduce bias into the data from an analytical reaction. For example, different template molecules can also be associated with context-dependent error profiles. For example, template sequences having certain characteristics can cause higher incidences of specific types of errors in a sequencing read produced during template-dependent nascent strand synthesis. A classic example in vivo is an increased incidence of duplications in highly repetitive regions of the genome. Likewise, sequencing reactions in vitro show that the behavior of a polymerase enzyme at a particular position on a template is influenced by the sequence context within which the particular position is found. Repeatedly sequencing the template to generate redundant sequence data can provide additional information to identify such errors. Since not every read is expected to have the error, multiple sequence reads of the same template can be analyzed to identify positions that differ between the reads, thereby identifying positions having errors in some of the reads. Additional methods for generating redundant sequence information that may be used with the methods, compositions, and systems provided herein are described in U.S. Pat. No. 7,476,503 and U.S. Patent Publication No. 20090029385, which are incorporated herein by reference in their entireties for all purposes.

Another strategy is to use sequence information generated from complementary templates, since the sequence context will be different in one of the complementary templates as compared to the other. For example, a double-stranded DNA template can be denatured and each strand sequenced separately. The sequence information from each complementary template is analyzed based upon the raw sequence data and the known sequence context effects on the sequencing method used. Since the sequence context is different for each template, the error profiles will be different for each, and this information can be used to produce a consensus sequence for the original template. Further, sensitivity to sequence context can be modulated by changing reaction conditions. As such, multiple sequencing reactions can be performed by a single sequencing enzyme under different reaction conditions, and the resulting sequence information analyzed based upon the raw sequence data and the known reaction condition effects on the sensitivity to sequence context of the sequencing enzyme used. As will be clear to one of ordinary skill, the use of repetitive sequence information from a single-stranded template and the use of complementary sequence information from both strands of a double-stranded template can be used in combination to determine consensus sequences.

In certain embodiments, single template molecules can be used to provide both repetitive and complementary sequence information, e.g., in a single-stranded circular template. For example, a double-stranded fragment can be modified to close the ends by annealing hairpins or stem-loop adapters to the ends. (See, e.g., U.S. Patent Publication No. 20090298075, incorporated herein by reference in its entirety for all purposes.) Upon separation of the duplex portion, e.g., by polymerase activity, heat, or other denaturing treatments, a single-stranded circle is formed that is appropriate for repeated, "rolling-circle" replication by a polymerase enzyme capable of strand displacement. Further, such methods typically involve immobilization of at least one component of the reaction, e.g., the template, enzyme, or primer.

Although certain embodiments of the invention are drawn to performing enzymatic reactions, e.g., single molecule sequencing reactions, it will be clear to those of ordinary skill in the art that these approaches are equally applicable to other analytical reactions that are sensitive to reaction conditions, e.g., antibody reactions, binding reactions, kinetic studies, and the like. Further, while many of the methods and compositions provided herein are described in terms of "single-molecule" analytical reactions, in which a single molecule or single molecular complex is monitored individually (e.g., in an optically resolvable configuration), it will be understood that the invention is not limited to such single molecule analytical reactions and in certain embodiments ensemble analytical reactions, such as microarray-based studies, also benefit from the teachings herein.

Platforms for ensemble analytical reactions include molecular array systems. For example, some such systems employ a number of immobilized binding agents that are each specific for a different binding partner. The different binding agents are immobilized in different known or readily determinable locations on a substrate, with each different binding agent immobilized in a patch of identical binding agents at a discrete location. There is no optical resolvability between binding agents in a patch, so when one performs an analytical reaction, binding events are detected for the patch as opposed to individual agents within the patch. When a binding partner (e.g., fluorescently labeled) is challenged against the array, the location to which the binding partner binds is indicative of its identity and/or the identity of the immobilized binding agent. Molecular array systems may be used to study protein-protein interactions, e.g., antibody/antigen, receptor-ligand interactions, chemical interactions, or more commonly nucleic acid hybridization interactions. See, U.S. Pat. Nos. 5,143,854, 5,405,783 and related patents, and GeneChip® systems from Affymetrix, Inc. They are also useful in certain nucleic acid sequencing systems, e.g., those that employ immobilized templates and a "flush-and-scan" methodology. For example, in some such methods, large numbers of template molecules can be provided in discrete locations on a planar substrate surface, such that the surface comprises multiple, small patches of identical template molecules. Blocked and labeled nucleotides are added separately (i.e., each type (A, G, C, or T) is added in the absence of the other three) and the template is monitored after each addition to determine if an incorporation event has occurred. Given the lack of optical resolvability between individually immobilized template molecules, each incorporation event is detected for the patch in an ensemble fashion. The sequence of incorporation events at a patch provides a nucleotide sequence corresponding to the templates immobilized within that patch. Reaction conditions can be altered in various ways in the performance of such ensemble-based analytical reactions, and the data collected under different reaction conditions analyzed to provide a final data set for the reaction as further described elsewhere herein. For example, a first ensemble-based sequence read detected under a first set of reaction conditions and a second ensemble-based sequence read detected under a second set of reaction conditions can be used to derive a final consensus sequence read using the known reaction behavior (e.g., error profile) under the first and second sets of reaction conditions.

In some embodiments of the invention, a template localizing moiety is used. As used herein, a "template localizing moiety" is a moiety comprising, e.g., a natural or synthetic polymer, such as a protein other than a polymerase, or any of the discrete materials described herein, that can associate with and/or retain a template nucleic acid (e.g., comprising DNA, RNA, or analogs or derivatives thereof) and fix it to, e.g., the surface on which the moiety itself has been immobilized. In some embodiments, a template localizing moiety can form a complex with a sequencing enzyme in a manner that permits the activity of the sequencing enzyme on the template. In some embodiments, a template localizing moiety can improve the processivity of a sequencing enzyme, and such moieties can include, e.g., a wide variety of DNA replication factors and/or DNA repair factors, as discussed hereinbelow. Although certain embodiments described herein are primarily focused on the use of localized template nucleic acids, it will be understood that not all embodiments described herein require template localization, and some embodiments benefit from immobilization of other reaction components, e.g., enzymes or primers.

In certain embodiments, sequencing of a single template molecule is monitored, preferably in real time, to generate a single sequencing read. However, decreases in the activity of individual sequencing enzyme molecules over time, can have a detrimental effect on the real time analysis of the activity of such sequencing enzymes, e.g., in a single-molecule sequencing reaction. In certain aspects, the present invention is directed to compositions, methods, systems and kits that can be beneficially used to localize a sequencing enzyme to a reaction region, e.g., a ZMW, without necessarily immobilizing the sequencing enzyme itself, within or proximal to the reaction region. For example, a template localizing moiety, e.g., that is capable of interacting with a sequencing enzyme, can be immobilized on a solid surface, e.g., on a surface, a well, or a single-molecule reaction region, and can be used to fix a nucleic acid template to the surface (see FIG. 1). For example, in certain preferred embodiments, the methods, compositions, and systems described herein are used with single-molecule sequencing technologies, in particular those described in U.S. Pat. Nos. 6,917,726 and 7,056,661; U.S. Ser. No. 12/767,673, filed Apr. 26, 2010; Published U.S. Patent Application Nos. 2010/0221716 and 2003/0044781; Eid, et al. (2009) Science 323:133-138; Levene et al. (2003) Science 299:682-686; and Korlach, et al. (2008) Nucleosides, Nucleotides and Nucleic Acids 27:1072-1083, all of which are incorporated herein by reference in their entireties for all purposes.

Although certain descriptions of the invention herein are primarily focused on template-dependent sequencing-by-synthesis methods that monitor incorporation of nucleotide bases into a nascent strand, it will be clear to one of ordinary skill upon review of the instant disclosure that the template localizing moieties can be used to immobilize template nucleic acids in myriad analytical reactions, including but not limited to exonuclease sequencing, pyrosequencing, nanopore-based sequencing, ligase-mediated sequencing, binding assays, and amplification-based methods. Enzymatic reactions are of special interest, in particular those that allow monitoring of the activity of a single enzyme molecule. In general, data from such a reaction is collected and analyzed, and the results from the analysis provide information about certain aspects of the reaction. In certain preferred embodiments, data collected is signal data related to a particular event of interest in the reaction, e.g., an event catalyzed by the enzyme. Such methods are known in the art and are further described, e.g., in WO/1994/023066; U.S. Pat. Nos. 5,516,633, 5,622,824, 5,750,341, 5,795,782, 5,969,119, 6,210,891, 6,258,568, 6,306,597, and 7,485,425; U.S. Ser. No. 61/186,661, filed Jun. 12, 2009; and U.S. Patent Publication Nos. 2007115205 and 20090131642, the disclosures of which are incorporated herein by reference in their entireties for all purposes.

As shown in FIG. 1, template localizing moiety 110 is immobilized within single molecule reaction region 100. Moiety 110 can fix template nucleic acid 120 to single molecule reaction region 100 to produce composition 130. In some embodiments of the compositions provided by the invention, the moiety topologically encircles the template, e.g., surrounds and encloses the template. For example, template localizing moiety 110 topologically encircles template 120 such that template 120 passes through moiety 110 not unlike a thread passes through the eye of a needle.

Figure 2:
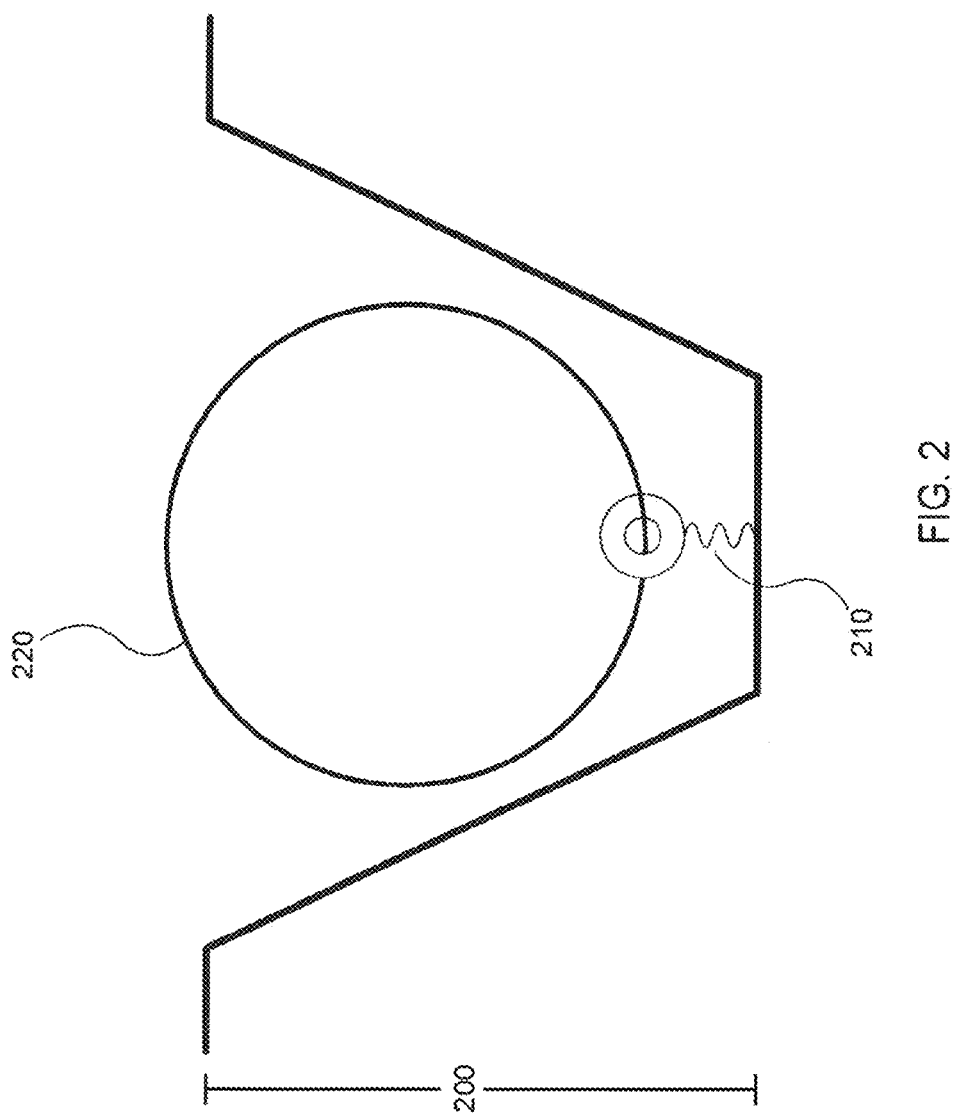
FIG. 2 provides a schematic depiction of a surface immobilized template localizing moiety that has fixed a closed nucleic acid loop within a single molecule reaction region.

The template nucleic acid of the compositions can be essentially any type of nucleic acid, e.g., a DNA or an RNA, single-stranded or double-stranded, linear or circular, genomic DNA, mRNA, rRNA, tRNA, artificial sequences, or combinations, analogs, or mimetics thereof. For example, a template nucleic acid can be linear (see FIG. 1) or, in preferred embodiments, it can be circular, e.g., form a "closed loop" wherein each nucleotide is covalently joined to the nucleotides preceding and following it (see FIG. 2). As shown in FIG. 2, template localizing moiety 210 topologically encircles circular template nucleic acid 220, fixing it within single molecule reaction region 200. Closed nucleic acid loops that are fixed within or proximal to a reaction region, e.g., a ZMW, through a surface-immobilized template localizing moiety will not diffuse out of the reaction region as readily as linear templates. This orientation of a template nucleic acid is particularly useful for certain redundant sequencing applications in which a single template is subjected to a sequencing reaction multiple times to generate multiple replicate nucleotide sequences that correspond (e.g., are identical or complementary) to the template nucleic acid. For example, a rolling-circle sequencing-by-synthesis reaction can be performed in which a polymerase capable of strand displacement repeatedly processes a circular template to synthesize a long, concatemeric nascent strand. The synthesis of the nascent strand is monitored to generate a long nucleotide sequence "read" for the nascent strand that contains multiple copies of a sequence complementary to the template strand, and this read is subjected to statistical analysis to determine the sequence of the template strand. Such rolling-circle synthesis can be used in other sequencing technologies, as well, such as pyrosequencing methods.

Figure 3:
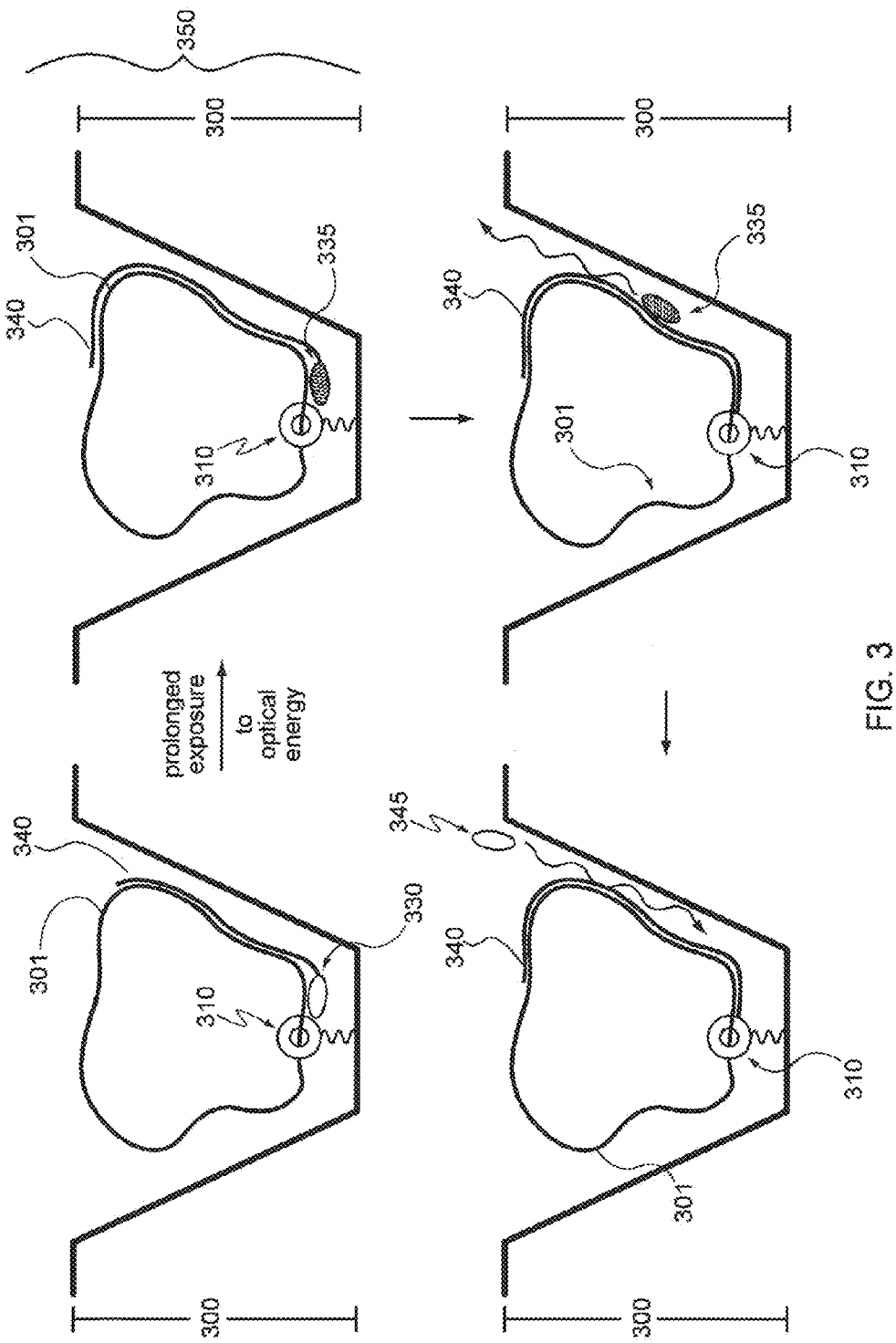
FIG. 3 depicts a template-directed synthesis reaction in which a first polymerase exchanges with a second polymerase without terminating the reaction.

Typically, single molecule sequencing-by-synthesis reactions take place in the presence of one or more fluorescently labeled nucleotides and/or nucleotide analogues, and fluorescent emissions from the fluorescent labels provide signal data during the course of the reaction. In general, the incorporation or release of the fluorescent label can be used to indicate the presence and composition of a growing nucleic acid strand, e.g., providing evidence of template-directed synthesis and/or the sequence of the nascent strand being synthesized, and by complementarity, the sequence of the template nucleic acid. As shown in FIG. 3, template localizing moiety 310, which has been immobilized within single molecule reaction region 300, has associated with and topologically encircled nucleic acid template 301, fixing it within the reaction region. Polymerase 330 can diffuse into the reaction region to initiate template-directed synthesis of a nascent strand that is complementary to at least a portion of a strand of template 301 to produce nascent strand 340. As used herein, a "nascent strand" is a nucleic acid molecule that is synthesized by a polymerase enzyme during the processing of a strand of a template nucleic acid. Although it is sometimes termed a "copy" of the template strand, the nascent strand actually comprises a sequence complementary to that of the strand of the template nucleic acid. Likewise, template-directed synthesis of a template nucleic acid is sometimes referred to as "replication" of the template nucleic acid, although the nascent strand synthesized is complementary rather than identical to the template nucleic acid. As such, one of ordinary skill will recognize that reference to "replication" of a template nucleic acid includes synthesis of a nascent strand complementary to the template strand. Further, immobilization of a template can also be accomplished by covalently and noncovalently attaching nucleic acids to a surface using methods well known in the art, e.g., streptavidin or avidin/biotin linkages, carbamate linkages, ester linkages, amide, thiolester, (N)-functionalized thiourea, functionalized maleimide, amino, disulfide, amide, hydrazone linkages, and among others. The template may be directly linked to the reaction site, or may be indirectly linked, e.g., through interaction with a primer or other moiety directly linked to the reaction site. Antibodies that specifically bind to nucleic acids can also be employed as the binding moieties. In addition, a silyl moiety can be attached to a nucleic acid directly to a substrate such as glass using methods known in the art. Various types of template localization strategies are provided, e.g., in U.S. Pat. Nos. 7,315,019, 5,143,854, and 5,405,783; U.S. Ser. No. 12/562,690, filed Sep. 18, 2009; and U.S. Patent Publication No. 20050042633, all of which are incorporated by reference in their entireties for all purposes. Similarly, such reactions can be carried out using a polymerase that is immobilized and, optionally, a template that is not. Methods for polymerase immobilization are described elsewhere herein. Preferably, immobilized templates, enzymes, and/or other reaction components are immobilized to produce individually resolvable molecular complexes that can be individually monitored during the reaction. Various methods of providing such individually resolvable configurations are known in the art, e.g., see European Patent No. 1105529 to Balasubramanian, et al.; Published International Patent Application No. WO 2007/041394; U.S. Patent Publication No. 2007-0238679, and U.S. Pat. Nos. 6,991,726, 7,013,054, 7,052,847, 7,033, 764, 7,056,661, 7,056,676, and 7,763,423, the full disclosures of which are incorporated herein by reference in their entireties for all purposes.

Over time, a polymerase's activity and fidelity can decrease. For example, prolonged exposure of a polymerase, e.g., polymerase 330, to the optical energy of the fluorescently labeled nucleotides or nucleotide analogues that are incorporated into a nascent and growing nucleic acid, e.g., nascent strand 340 can reduce the enzyme's processivity, accuracy, and polymerase activity over time (see composition 350, which includes inactive polymerase 335). Other environmental factors that can lead to polymerase inactivation include, e.g., oxidation, degradation, and the like. Inactive polymerase 335 dissociates from the template 301 and can exchange with active polymerase 345 without terminating the sequencing read, e.g., the polymerase-mediated processing of template 301 can reinitiate upon association with a second polymerase, e.g., active polymerase 345, to the immobilized template 301. Typically, nascent strand 340 remains in single molecule reaction region 300 during such a polymerase exchange so that active polymerase 345 can continue incorporating nucleotides into nascent strand 340, e.g., using 301 as a template. In certain embodiments, nascent strand 340 can be removed from template 301 prior to reinitiation of template-directed synthesis by active polymerase 345, e.g., by heat-denaturation, chemical treatment, high salt concentration, etc. Since nascent strand 340 is held in reaction region 300 only by association with template nucleic acid 301, disruption of that association facilitates removal of nascent strand 340 from reaction region 300. Polymerase 330 and polymerase 345 can be the same type of polymerase, or can be two different types of polymerases having different characteristics, e.g., rates of incorporation, rates of translocation, fidelities, processivities, specificities, retention time for nucleotides or nucleotide analogs in the active site, error profiles, pulse characteristics, etc.

Figure 4:
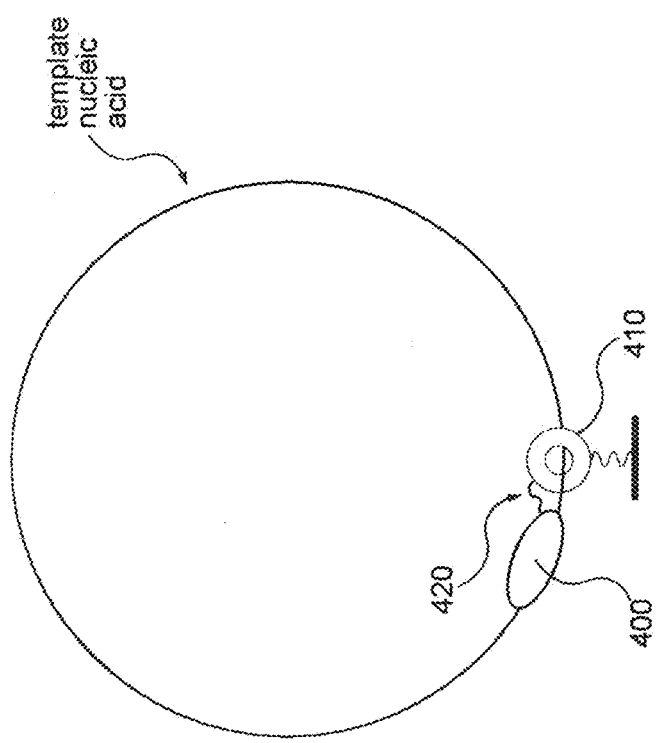
FIG. 4 provides a schematic depiction of an alternate embodiment of the compositions in which a polymerase is covalently bound to a surface-immobilized template localizing moiety.

Optionally, a template localizing moiety can also form a complex with a sequencing enzyme, e.g., to bring the sequencing enzyme to a portion of the template that is at a reaction site and/or within an observation (or detection) volume. For example, in certain embodiments of the compositions (see FIG. 4), a polymerase, e.g., polymerase 400 can be covalently attached to the surface-immobilized template localizing moiety, e.g., moiety 410, e.g., via the polymerase's C-terminal end, e.g., polymerase C-terminal end 420. Alternatively, an exonuclease can be brought into proximity to a terminal portion of a template nucleic acid. However, in preferred embodiments of the compositions, a sequencing enzyme associates with the moiety in a non-covalent manner. Optionally, a sequencing enzyme can bind the template tethering moiety via a reversibly cleavable linker, e.g., a linker that can reform with a new sequencing enzyme. This permits the sequencing enzyme to exchange with other sequencing enzymes present, e.g., in a sequencing reaction mix, without terminating the sequencing reaction. In yet further embodiments, a sequencing enzyme can be covalently or non-covalently attached to a linker bound to the surface, and in certain preferred embodiments such a linker is a cleavable linker that allows release of a sequencing enzyme, e.g., to facilitate exchange with another sequencing enzyme in the reaction mixture. In certain embodiments in which a multisubunit sequencing enzyme is used, all or only one or a subset of subunits can be attached to the template localizing moiety and/or the surface. For example, HIV reverse transcriptase is a heterodimer and only one of the subunits need be attached to the template localizing moiety and/or surface in order to maintain the enzyme at the reaction site. A reversible attachment, e.g., a photocleavable linker, can be used to facilitate sequencing enzyme exchange during the course of the reaction.

Certain compositions of the invention include a surface-immobilized template localizing moiety, rather than a surface-immobilized sequencing enzyme, to localize a sequencing reaction, e.g., template-directed synthesis or exonuclease degradation reaction, to a defined reaction region. Sequencing reactions that include the provided compositions, e.g., compositions in which a first, e.g., less active or inactive, sequencing enzyme can be exchanged with a second, e.g., active, sequencing enzyme, are not terminated when a sequencing enzyme's activity, specificity, accuracy, processivity, and fidelity decreases, e.g., as a result of the exposure to optical energy of fluorescently labeled nucleotides and/or nucleotide analogs. For example, different enzymes having complementary characteristics (e.g., complementary error profiles) may be chosen for use in a single reaction. In certain embodiments, a first enzyme with a first error profile is initially used to sequence the template, and is subsequently exchanged with a second enzyme having a second error profile. The sequence data resulting from processing the template with the two different enzymes is analyzed, and the complementary error profiles serve to identify and "cancel out" errors introduced into the sequencing reads generated using each polymerase. Alternatively or in addition, different enzymes having complementary characteristics (e.g., complementary error profiles) may be chosen for use in multiple independent reactions using identical templates and/or complementary templates, e.g., at different reaction regions on a single substrate. As a result, the methods and systems of the invention, in which the compositions described above can be used, can beneficially increase sequence throughput and improve the accuracy of sequence data, e.g., through generation of redundant sequence information from a single template or a plurality of identical and/or complementary templates. Moreover, the invention can advantageously lower fabrication and reagent costs (see FIG. 1). For example, an array of single molecule reaction volumes in which individual sequencing enzymes have been immobilized is no longer useful after the sequencing enzymes have become inactive. However, an array of single molecule reaction regions in which individual templates have been immobilized, e.g., via template localizing moieties, e.g., FIG. 1, array 140, can be used repeatedly and continuously under the same or changing reaction conditions, e.g., by the same or different polymerases, using the same or different types of nucleotides (or analogs thereof), under varying pH conditions, using different buffers, using varying temperatures, using different divalent cations or concentrations thereof, using different illumination frequencies, power, intensities, and/or wavelengths, and the like. In doing so, the same individual templates can be sequenced multiple times under the same or different conditions.

Further, in embodiments in which the sequencing enzyme is not tethered to the surface or the template localizing moiety, the sequencing enzyme activity may be enhanced by virtue of the lack of a physical linkage to the sequencing enzyme. For example, a polymerase enzyme that is free in solution is not hindered by being directly tethered to a surface or template localizing moiety, which may interfere with conformational changes required for template-directed synthesis, e.g., due to torsional stress, electrostatic interference, or steric hindrance caused by the linking moiety, potentially causing a decrease in activity, processivity, or accuracy of the enzyme. Further, a polymerase that is free in solution can be a more "natural" polymerase than a polymerase comprising structural alterations required for binding to the surface. In addition, a potential source of experimental variation is eliminated since there can be no variation due to differences in sequencing enzyme immobilization chemistry between different reaction sites on the same or different surfaces.

Further Details Regarding Template Localizing Moieties

Certain compositions of the invention rely on a surface-immobilized template nucleic acid, e.g., bound to a template localizing moiety, rather than a surface-immobilized polymerase, to localize a sequencing reaction, e.g., template-directed synthesis or exonuclease sequencing reaction, to a defined reaction region. This configuration can beneficially increase read lengths and improve the accuracy of the sequencing data produced by, e.g., a single molecule sequencing reaction, as it permits the exchange of a first (e.g., inactive, photodamaged, mismatch error-prone, insertion error-prone, deletion error-prone, non-processive, etc.) sequencing enzyme with a second (e.g., active, non-photodamaged, differently error-prone, processive, etc.) sequencing enzyme, e.g., present in a sequencing reaction mix, without terminating nucleic acid sequencing. For example, a template-directed synthesis reaction can proceed anew when an active polymerase replaces a polymerase, e.g., whose activity has decreased as a result of prolonged exposure to the optical energy of fluorescently labeled nucleotides and/or nucleotide analogs in the sequencing reaction mix.) Advantageously, the compositions of the invention can decrease reagent use and lower the fabrication costs of, e.g., ZMW arrays used in high-throughput single-molecule sequencing systems.

In some aspects, a template localizing moiety can comprise, e.g., a polymer, and/or any discrete material that can be coupled/associated, at least temporarily, to or with a nucleic acid, e.g., a DNA or an RNA. Such a polymer can comprise natural structural units (e.g., nucleotides, amino acids, sugars, etc.), or synthetic structural units (e.g., styrene, ethylene, propylene, etc.), or modifications and/or combinations thereof. For example, such a polymer can comprise one or more polynucleotides, polypeptides, polysaccharides, polystyrene, polyethylene (e.g., polyethylene glycol, Spacer 18, etc.), polypropylene, polymer beads, silica beads, ceramic beads, glass beads, magnetic beads, metallic beads, and organic resin beads can be used to localize a template nucleic acid to a defined reaction region. Such template localizing moieties can have essentially any shape, e.g., spherical, helical, spheroid, rod shaped, cone shaped, disk shaped, cubic, polyhedral or a combination thereof. In preferred embodiments, the template localizing moiety topologically encircles the template nucleic acid. Optionally, the shape of a template localizing moiety can also be used to orient the moiety in the relevant well, e.g., to ensure that the immobilized nucleic acid is accessible to a sequencing enzyme and can be used as a template in, e.g., a sequencing reaction. Template localizing moieties can optionally be coupled to any of a variety of reagents that facilitate surface attachment of the nucleic acid, e.g., a DNA or an RNA. For example, such reagents include but are not limited to streptavidin or avidin/biotin linkages, carbamate linkages, ester linkages, amide, thiolester, (N)-functionalized thiourea, functionalized maleimide, amino, disulfide, amide, hydrazone linkages, and others known in the art.

In certain preferred embodiments, a template localizing moiety can function not only to localize the template to a reaction region, but also to effectively trap the sequencing enzyme in the observation or detection volume of the reaction region. Take, for example, a template localizing moiety large enough to allow passage of a template, but too small to allow passage of a polymerase. Upon encountering the template localizing moiety, a polymerase translocating on the template would be spatially constrained at the template localizing moiety due to the inability to "follow" the template through the template localizing moiety. Therefore, continued translocation along the template would require the template be pulled through the template localizing moiety by the polymerase enzyme. Such template localizing moieties can comprise various types of polymers, including but not limited to polynucleotides, polypeptides, polysaccharides, and other synthetic polymers. Specific examples using such template localizing moieties comprising polynucleotides and combinations of natural and synthetic polymers are provided below. Those skilled in the art will be familiar with configurations that possess this feature, which are described in the art, e.g., see publications related to the use of nanopores from Jene Golovchenko and/or Amit Meller, as well as Turner, et al. (2002) Phys Rev Lett 88(12): 128103, the disclosures of which are incorporated herein by reference in their entireties for all purposes.

Template localizing moieties of the invention can essentially be any discrete material that can be immobilized, e.g., on a planar surface, in a well, or in a single molecule reaction region, e.g., a ZMW. Desirably, the material(s) that comprises a template localizing moiety permit the moiety to associate with a template in such a manner that maintains or increases a sequencing enzyme's processivity, e.g., in degrading the template or performing template-directed nascent strand synthesis. Examples of such materials can include polymer beads or particles (e.g., polystyrene, polypropylene, latex, nylon and many others), silica or silicon beads, ceramic beads, glass beads, magnetic beads, metallic beads and organic compound beads. An enormous variety of particles that can be used to fix a template to or near a defined reaction region are commercially available, e.g., those typically used for chromatography (see, e.g., Catalogs from Sigma-Aldrich (Saint Louis, Mo.), Supelco Analytical (Bellefonte, Pa.; sold, e.g., through Sigma-Aldrich), as well as those commonly used for affinity purification (e.g., the various magnetic Dynabeads™, which commonly include coupled reagents) supplied e.g., by Invitrogen. For a discussion of matrix materials see also, e.g., Hagel et al. (2007) *Handbook of Process Chromatography, Second Edition: Development, Manufacturing, Validation and Economics*, Academic Press; 2nd edition ISBN-10: 0123740231; Miller (2004) *Chromatography: Concepts and Contrasts* Wiley-Interscience; 2nd edition ISBN-10: 0471472077; Satinder Ahuja (2002) *Chromatography and Separation Science (SST)* (*Separation Science and Technology* Academic Press, ISBN-10: 0120449811; Weiss (1995) *Ion Chromatography* VCH Publishers Inc.; Baker (1995) Capillary Electrophoresis John Wiley and Sons; Marcel Dekker and Scott (1995) *Techniques and Practices of Chromatography* Marcel Dekker, Inc.

In preferred embodiments of the compositions described herein, a template localizing moiety comprises a polypeptide, preferably a protein other than a polymerase used to synthesize a polynucleotide complementary to the template nucleic acid, that can be attached to, e.g., a planar surface, a well, or a single-molecule reaction region, e.g., a ZMW, in an orientation that preserves its nucleic acid-binding activity and, optionally, its sequencing enzyme binding activity, wherein the protein is configured to form a complex with a sequencing enzyme. Proteins that can optimally be used as template localizing moieties in the methods, compositions, systems, and kits of the invention include a wide variety of DNA replication factors, DNA repair factors, and/or transcription factors e.g., a processive nuclease, a single-strand binding protein (SSBP), a helicase, a DNA repair enzyme, a polymerase mutant, fragment, or subunit thereof that lacks nascent strand synthesis activity but is able to translocate along a template nucleic acid, a DNA processivity factor, e.g., a helicase, or a protein that non-specifically binds a double-stranded nucleic acid—essentially any protein or protein mutant that can associate with a template nucleic acid and not interfere with an ongoing sequencing reaction. For example, human oxoguanine DNA glycosylase 1 (hOgg1), which is a DNA glycosylase/apurinic (AP) lyase (see, e.g., Klungland, et al. (2007) DNA Repair (Amst) 6(4): 481-8, which is incorporated herein by reference in its entirety for all purposes) or homologs thereof, including yeast Ogg proteins (e.g., yOgg1 or yOgg2), *E. coli* Mut proteins (e.g., MutM (FPG protein), and others known in the art. Further, multiple such proteins may be bound at a single reaction site to immobilize a single template molecule.

As described above, a template localizing moiety of the compositions preferably fixes a template nucleic acid to, e.g., a single molecule reaction region by topologically encircling the template (see, e.g., FIG. 2 and corresponding description). For example, DNA polymerase sliding clamp proteins can be beneficially included in the compositions of the invention. Sliding clamps are a family of multimeric ring-shaped DNA polymerase processivity factors that play essential roles in DNA metabolism (reviewed in, e.g., Barsky, et al. (2005) "DNA sliding clamps: just the right twist to load onto DNA." *Curr Biol* 15: R989-92 and Indiani, et al. (2006) "The replication clamp-loading machine at work in the three domains of life." *Nat Rev Mal Cell Biol* 7: 751-761). Sliding clamp proteins have been identified in Bacteria, e.g., the β clamp of *E. coli* DNA polymerase III; Archea, e.g., archeal PCNA; and Eukarya, e.g., eukaryal PCNA; as well as in viruses and phages, e.g., T7 gp45.

Though they share little amino acid sequence homology, sliding clamps from Bacteria, Archea, and Eukaryotes have similar three-dimensional structures (Kelman, et al. (1995) "Structural and functional similarities of prokaryotic and eukaryotic DNA polymerase sliding clamps." *Nucl Acid Res* 23: 3613-3620; Iwai, et al. (2000) "Phylogenetic analysis of archaeal PCNA homologues." *Extremophiles* 4: 357-364; and Hingorani, et al. (2000) "A tale of toroids in DNA metabolism." *Nat Rev Mol Cell Biol* 1: 22-30). Sliding clamps comprise 2-3 monomers to yield a ring comprised of six domains. Each ring has similar dimensions and a central cavity large enough to accommodate a duplex DNA molecule (Kelman, et al. (1995) "Structural and functional similarities of prokaryotic and eukaryotic DNA polymerase sliding clamps." *Nucl Acid Res* 23: 3613-3620 and Hingorani, et al. (2000) "A tale of toroids in DNA metabolism." *Nat Rev Mol Cell Biol* 1: 22-30).

Sliding clamp proteins are typically assembled around double-stranded DNA by a clamp loading complex (reviewed in O'Donnell, et al. (2002) "Clamp loaders and sliding clamps." *Curr Opin Struct Biol* 12: 217-224) in an ATP-dependent reaction. Following assembly, sliding clamps can slide bidirectionally along the duplex (Stukenberg, et al. (1991) "Mechanism of the sliding beta-clamp of DNA polymerase 111 holoenzyme." *J Biol Chem* 266: 11328-11334). Clamp proteins bind DNA polymerase and act as mobile tethers that prevent the enzyme from dissociating from a template DNA strand. Because a rate limiting step in DNA replication is the association of the polymerase with the DNA template, the presence of a sliding clamp can be beneficially increases the number of, e.g., fluorescently labeled nucleotides that the polymerase can add to the growing strand per association event during, e.g., a sequencing reaction, thus increasing read length.

Additional details regarding sliding clamp proteins, clamp loading complexes, and the DNA polymerases with which they interact are elaborated in, e.g., Georgescu, et al. (2008) "Structure of a Sliding Clamp on DNA." *Cell* 132: 43-54; Seybert, et al. (2004) "Distinct roles for ATP binding and hydrolysis at individual subunits of an archaeal clamp loader." *EMBO J* 23: 1360-1371; Bruck, et al. (2001) "The ring-type polymerase sliding clamp family." Genome Biol 2: reviews3001.1-reviews3001.3; Johnson, et al. (2005) "Cellular DNA replicases: components and dynamics at the replication fork." *Annu Rev Biochem* 74: 283-315; and Vivona, et at (2003) "The diverse spectrum of sliding clamp interacting proteins." *FEBS Lett* 546:167-72. An artificial processivity clamp that can be bound to surfaces has recently been described in, e.g., Williams, et at (2008) "An artificial processivity clamp made with streptavidin facilitates oriented attachment of polymerase-DNA complexes to surfaces." *Nucl Acids Res doi:* 10.1093/nar/gkn531.

Hexameric helicases are another class of template localizing moieties that can be beneficially included in the methods, compositions, kits, and systems of the invention to, e.g., fix a template nucleic acid to a surface. Helicases can also form a processive complex with a DNA polymerase during processing of the template in, e.g., a sequencing reaction. Hexameric helicases, e.g., *E. coli* DnaB and Rho, T4 gp41, and T7 gp4, are a class of NTP-dependent motor proteins that play a role DNA metabolism. Hexameric helicases have a characteristic ring-shaped structure, and these enzymes typically move along the phosphodiester backbone of the nucleic acid to which they are bound, using the energy produced by nucleic acid-stimulated NTP hydrolysis to translocate along the nucleic acid while catalyzing the unidirectional, processive separation of two strands of a complementary nucleic acid duplex. Recent structural studies have indicated that a single strand of a DNA duplex passes through the hexamer channel (Enemark, et al. (2006) "Mechanism of DNA translocation in a replicative hexameric helicase," *Nature* 442 270-275).

A hexameric helicase can optimally be used with a non-processive, non-strand-displacing polymerase, e.g., a Klenow fragment, in, e.g., a sequencing reaction. In certain embodiments that include a hexameric helicase, the concentration of NTP present in, e.g., a sequencing reaction mix, can modulate the rate at which the helicase catalyzes the unwinding of a double-stranded DNA template. This, in turn, can modulate the sequencing rate of, e.g., a non-strand displacing polymerase in a template-directed synthesis reaction.

Further details regarding hexameric helicase translocation mechanisms; hexameric helicase base pair separation mechanisms; and/or assays to measure helicase translocation rate or processivity are elaborated in, e.g., Enemark, et al. (2008) "On helicases and other motor proteins." *Curr Opin Struct Biol* 18: 243-57, Epub March 2008; Sclafani, et al. (2004) "Two heads are better than one: regulation of DNA replication by hexameric helicases." *Genes Dev,* 18: 2039-2045; Patel, et al. (2000) "Structure and function of hexameric helicases." *Annu Rev Biochem* 69: 651-697; and Xie (2006) "Model for helicase translocating along single-stranded DNA and unwinding double-stranded DNA." *Biochim Biophys Acta* 1764:1719-29, Epub 2006 Sep. 26.

In preferred embodiments of the compositions described herein, a template localizing moiety comprises a polynucleotide, i.e., a polynucleotide other than the template, that can be attached to, e.g., a planar surface, a well, or a single-molecule reaction region, e.g., a ZMW, in an orientation that allows it to constrain a template to which it is initially annealed even after it has been displaced from the template, e.g., by a translocating polymerase enzyme on the template. Polynucleotides that can optimally be used as template localizing moieties in the methods comprise a central region that is complementary to at least one region of the template to be immobilized and two end regions that associate with a surface of a reaction region such that when bound to the surface the template localizing moiety loops over and optionally completely around the template, thereby localizing it to the reaction site. The template can move through the loop(s) formed by the template localizing moiety, but cannot diffuse away from the reaction region unless either an end of the template localizing moiety is dissociated from the reaction region or an end of the template passes through the loop. As such, although linear templates can be used with such polynucleotide template localizing moieties, in certain embodiments a circular template is preferred since a circular template can be repeatedly processed at a reaction region without "slipping out" of the template localizing moiety. Further, if a polymerase dissociates from the template nucleic acid, a second polymerase can bind the template and continue template-directed synthesis using the same template nucleic acid at the same reaction region. Since the polymerase is not covalently tethered, it can readily dissociate and exchange with another polymerase in the reaction mixture. As such, a damaged polymerase can be replaced by an undamaged polymerase, thereby allowing stalled synthesis to continue on the same template nucleic acid. Alternatively, polymerases having different characteristics (e.g., processivities, specificities, fidelities, activities, error profiles, affinities, etc.) can be exchanged during the reaction to permit collection of sequencing data using more than one kind of polymerase. For example, data collected from a sequencing reaction using a highly processive but error-prone polymerase can be combined with data collected after exchanging this polymerase with a less processive but highly accurate polymerase. In other embodiments, data collected from a sequencing reaction using a deletion error-prone polymerase that rarely produces insertion errors can be combined with data collected after exchanging the deletion error-prone polymerase with an insertion error-prone polymerase that rarely produces deletion errors. Data generated by template-directed synthesis using a single template nucleic acid by multiple polymerases can thereby be generated and collected sequentially, and subjected to statistical analysis to determine a sequence of the template nucleic acid. For example, sequence data comprising complementary error profiles of two different polymerases allow identification and correction of polymerase-dependent errors in the sequencing reads, thereby facilitating construction of a highly accurate consensus sequence for the template nucleic acid.

A strand of double-stranded DNA usually circles the axis of the double helix once every 10.4 base pairs. As such, in certain aspects, a template localizing moiety comprises a polynucleotide portion that is complementary to at least about ten or more adjacent nucleotides to ensure that the complementary region wraps around the template strand at least one time. In certain embodiments, the complementary region is longer to create multiple loops around the template strand. Further, in certain preferred embodiments, one or more loops formed by a template localizing moiety around a template nucleic acid block passage of a polymerase enzyme translocating on the template, effectively localizing the polymerase to the template at the template localizing moiety. This can serve to position the polymerase at a desired location within a reaction region, e.g., in the observation volume. This aspect is especially useful for large template nucleic acids that extend outside the observation volume.

A further advantage provided by a template localizing moiety comprising a portion complementary to a template nucleic acid is the ability to selectively immobilize a subset of template nucleic acids having one or more particular polynucleotide sequences of interest (e.g., exonic or intronic regions, regulatory regions, and the like). For example, a whole genomic sample can be fragmented and mixed with a pool of template localizing moeties having polynucleotide regions complementary to a set of genetic loci known to predict susceptibility to a given disease. Only genomic fragments having one or more of those genetic loci of interest will be targeted and immobilized by the template localizing moieties, and subsequently subjected to sequence analysis. This strategy significantly reduces the amount of data generated, and therefore the amount of statistical analysis required for determining the relevant genotypes for an individual, and by association, their susceptibility to the given disease.

Figure 5:
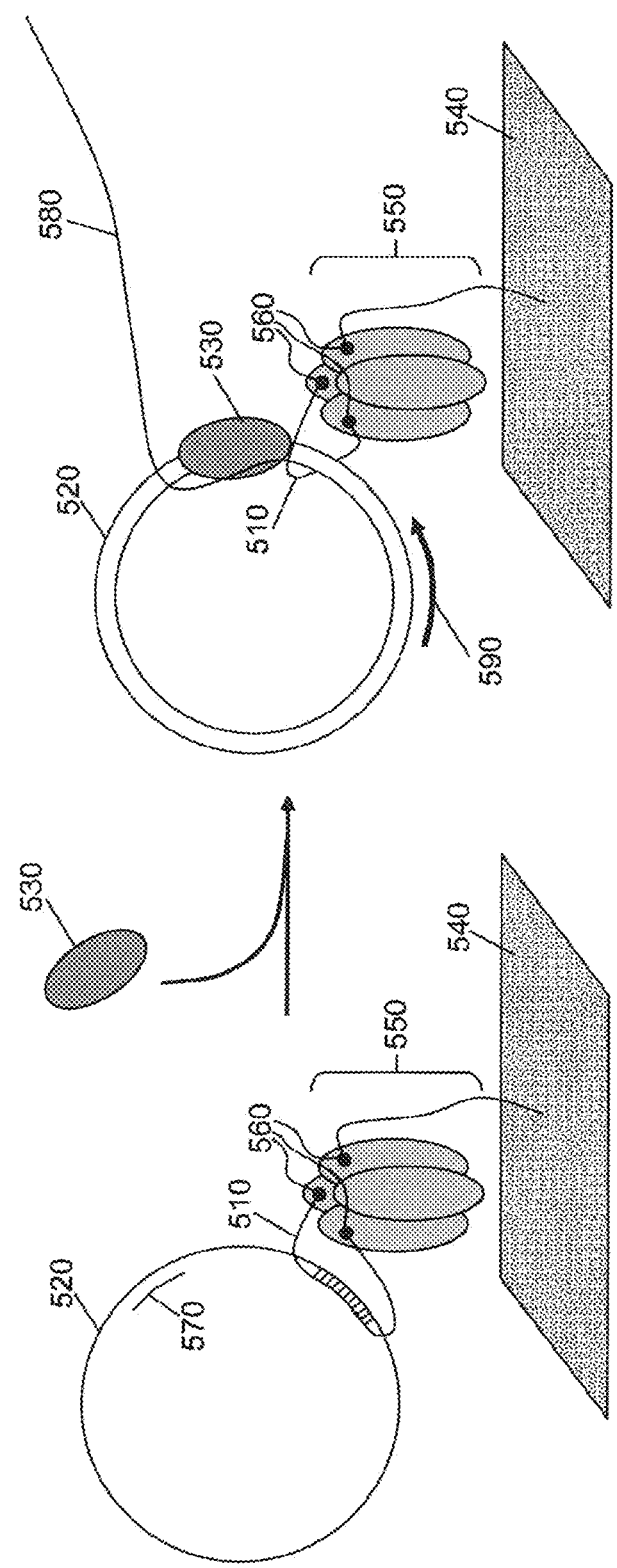
FIG. 5 provides a schematic depiction of a polynucleotide-containing template localizing moiety that is complementary to a region of a single-stranded, circular template nucleic acid and that forms a single loop over the template upon dissociation.

FIG. 5 provides an exemplary embodiment of a polynucleotide-containing template localizing moiety 510 that comprises a polynucleotide region complementary to a region of a single-stranded, circular template nucleic acid 520 long enough to loop over the template nucleic acid 520 one time. The ends of the template localizing moiety 510 are derivatized with biotin 560 to promote binding of the ends of the template localizing moiety 510 to the streptavidin tetramer 550. The template localizing moiety 510 is annealed to the template nucleic acid 520, and is subsequently immobilized on a substrate 540 via interaction with a streptavidin tetramer 550 bound to a biotin-derivatized surface of the substrate 540. The template nucleic acid 520 is also annealed to primer 570, and subsequently exposed to a polymerase 530. Binding of polymerase 530 to the complex results in extension of the primer 570 as the polymerase translocates along the template nucleic acid 520, producing a nascent polynucleotide strand 580. Upon displacement of the complementary region of the template localizing moiety 510, a single loop is formed that passes over the template nucleic acid 520, thereby localizing it to the reaction region on the substrate 540. Arrow 590 shows the direction of movement of the template strand 520 toward the polymerase 530 during translocation when the polymerase 530 is blocked by the template localizing moiety 510. Although FIG. 5 illustrates an embodiment in which a single subunit of the streptavidin tetramer 550 is linked to the surface and two are linked to the template localizing moiety 510, further embodiments include utilization of the fourth subunit, e.g., to link to the surface, the sequencing enzyme, or other components of a reaction mixture, including but not limited to elongation factors, components of a detection system (e.g., luciferase/sulfurylase), etc.

Figure 6:
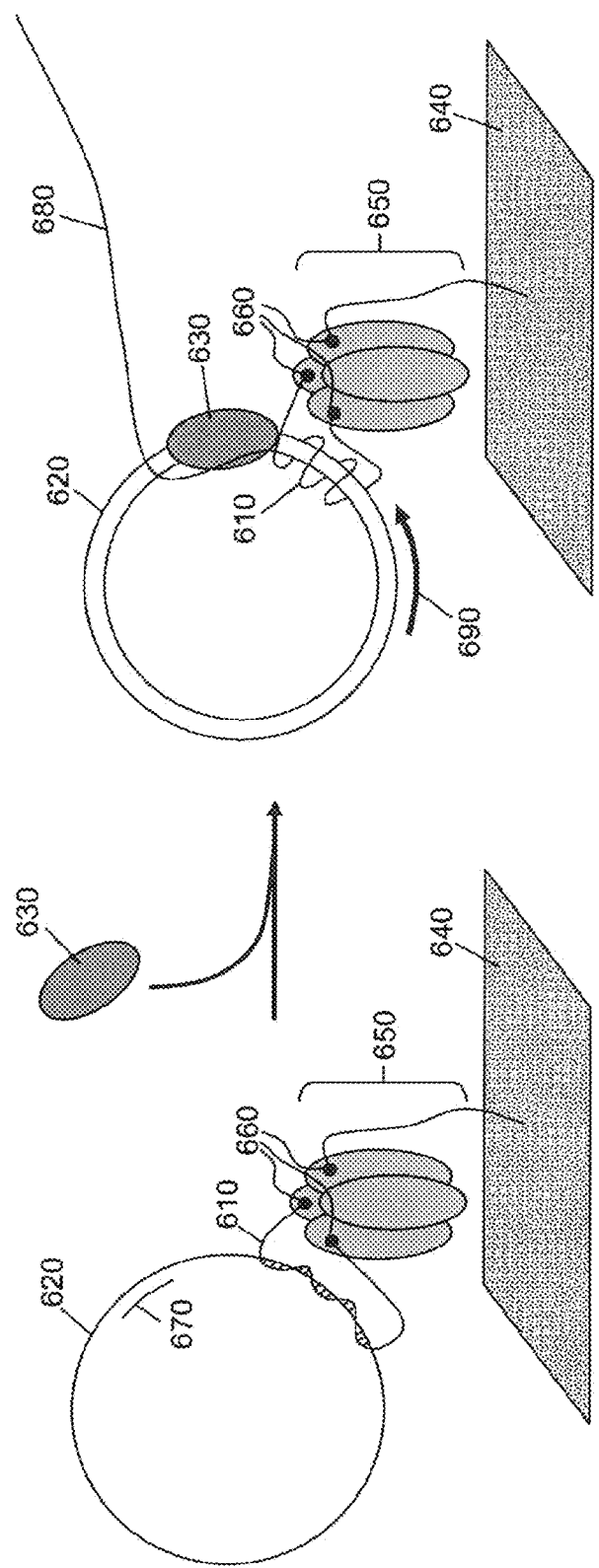
FIG. 6 provides a schematic depiction of a polynucleotide-containing template localizing moiety that is complementary to a region of a single-stranded, circular template nucleic acid and that forms multiple loops around the template upon dissociation.

FIG. 6 provides an exemplary embodiment of a polynucleotide-containing template localizing moiety 610 that comprises a polynucleotide region complementary to a region of a single-stranded, circular template nucleic acid 620 long enough to loop over the template nucleic acid 620 three times. The ends of the template localizing moiety 610 are derivatized with biotin 660 to promote binding of the ends of the template localizing moiety 610 to the streptavidin tetramer 650. The template localizing moiety 610 is annealed to the template nucleic acid 620, and is subsequently immobilized on a substrate 640 via interaction with a streptavidin tetramer 650 bound to a biotin-derivatized surface of the substrate 640. The template nucleic acid 620 is also annealed to primer 670, and subsequently exposed to a polymerase 630. Binding of polymerase 630 to the complex results in extension of the primer 670 as the polymerase translocates along the template nucleic acid 620, producing a nascent polynucleotide strand 680. Upon displacement of the complementary region of the template localizing moiety 610, a single loop is formed that passes over the template nucleic acid 620, thereby localizing it to the reaction region on the substrate 640. Arrow 690 shows the direction of movement of the template strand 620 toward the polymerase 630 during translocation when the polymerase 630 is blocked by the template localizing moiety 610.

Figure 7:
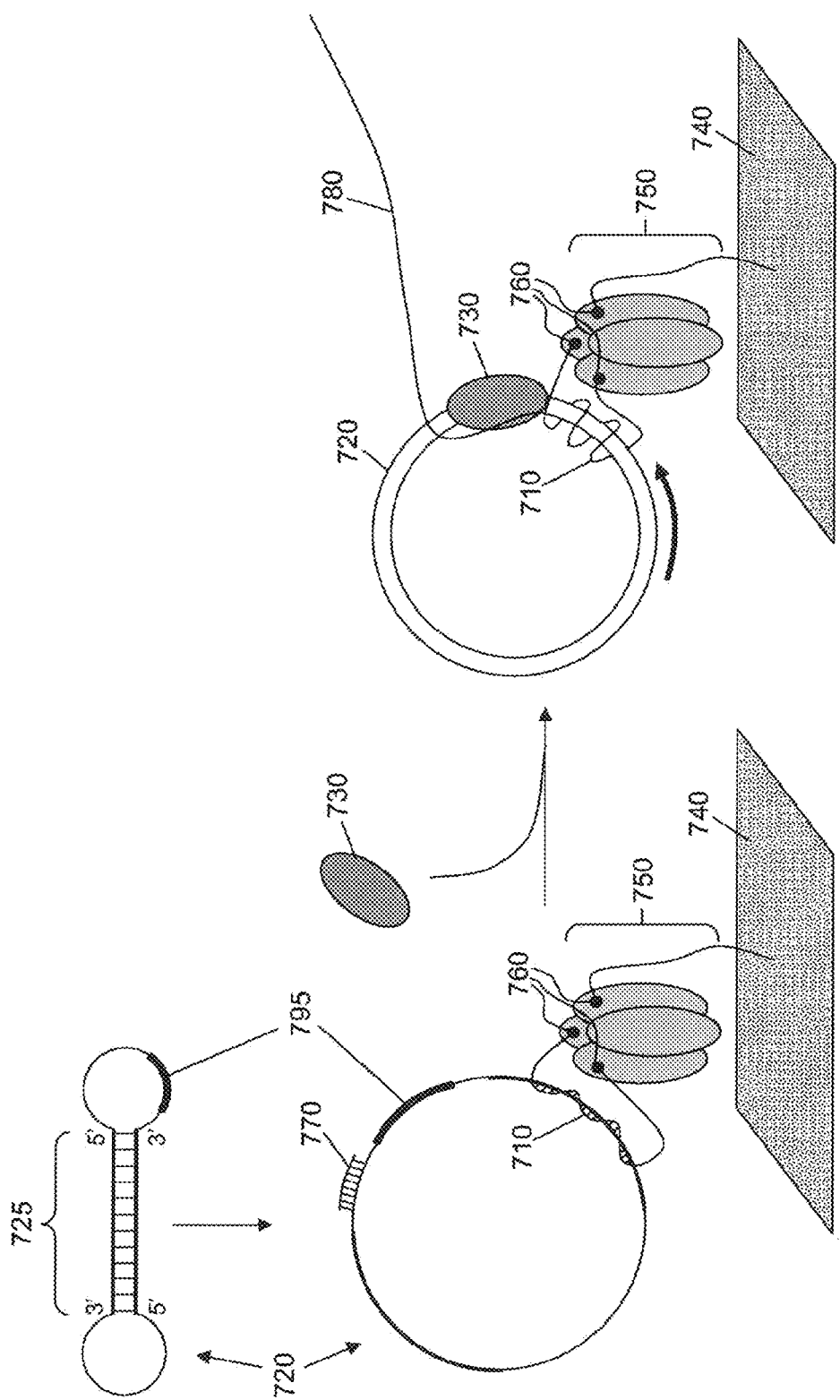
FIG. 7 provides a schematic depiction of a polynucleotide-containing template localizing moiety that is complementary to a region of a template nucleic acid that comprises regions of internal complementarity.

FIG. 7 provides an exemplary embodiment of a polynucleotide-containing template localizing moiety 710 that comprises a polynucleotide region complementary to a region of a single-stranded, circular template nucleic acid 720 long enough to loop over the template nucleic acid 720 three times. However, unlike the embodiment depicted in FIG. 6, the template nucleic acid 720 comprises regions of internal complementarity (shown as double-stranded region 725), such that it can form a partially double-stranded template nucleic acid. The ends of the template localizing moiety 710 are derivatized with biotin 760 to promote binding of the ends of the template localizing moiety 710 to the streptavidin tetramer 750. Primer 770 and template localizing moiety 710 are annealed to template nucleic acid 720, e.g., following heat-denaturation. In some preferred embodiments, template localizing moiety 710 is annealed to one strand within the duplex region of the template nucleic acid 720. The resulting annealed complex is subsequently immobilized on a substrate 740 via interaction with the streptavidin tetramer 750 bound to a biotin-derivatized surface of the substrate 740. The template nucleic acid 720 is subsequently exposed to a polymerase 730, which extends primer 770 as the polymerase translocates along the template nucleic acid 720, separating any duplex regions in its path and producing a nascent polynucleotide strand 780. Upon displacement of the complementary region of the template localizing moiety 710, three loops are formed that pass over the template nucleic acid 720, thereby localizing it to the reaction region on the substrate 740. Arrow 790 shows the direction of movement of the template strand 720 toward the polymerase 730 during translocation when the polymerase 730 is blocked by the template localizing moiety 710 looped around the template nucleic acid.

In some embodiments, the template nucleic acid 720 comprises a tag sequence 795 in the single-stranded region that can be used to identify certain characteristics of the template nucleic acid 720, e.g., source information. For example, a genomic DNA sample can be fragmented to produce a set of double-stranded DNA fragments, and each fragment can be linked to two single-stranded hairpins, one at each end. A tag sequence incorporated into at least one of the hairpin structures contains a nucleotide sequence that identifies the source (e.g., individual, species, subspecies, experimental/clinical group, etc.) from which the genomic DNA was isolated. Such tag sequences allow pooling of samples from various sources where the sample from each source is differentially tagged. During sequence analysis, the identification of a particular tag sequence in the sequencing read is used to deconvolute the pooled sequencing data and identify the particular source of the sample. Such tag sequences (also termed "bar codes" or "registration sequences") and partially double-stranded template nucleic acids are further described in U.S. patent application Ser. No. 12/413,258, filed Mar. 27, 2009, which is incorporated herein by reference in its entirety for all purposes.

Although described above primarily in terms of biotin-streptavidin linkages, a polynucleotide template localizing moiety can be derivatized at each end with other entities that preferentially associate with a molecule immobilized at a reaction region. For example, each end of a template localizing moiety can be derivatized with a chemically active linkage including but not limited to "Click Chemistry" (Kolb, et al. (2001) Angew. Chem. Int. Ed. 40:2004-2021; and CLIP- and SNAP-tag strategies (New England BioLabs, Inc.). Further, a variety of surface attachment strategies can be used, including disulfide bond formation, amine linkages through an activated carbonyl, reactive groups on a number of siloxane functionalizing reagents (described elsewhere herein), and the like.

In certain preferred embodiments, a template localizing moiety that comprises a polynucleotide portion that is complementary to a template nucleic acid also comprises one or more polynucleotide portions that are not complementary to the template nucleic acid and/or one or more portions that do not comprise polynucleotides. In certain embodiments, one or more ends of the complementary portion may be linked to non-complementary portions, e.g., poly-T, poly-A, and the like. In other embodiments, a complementary polynucleotide portion may be flanked by portions comprising synthetic structural units, e.g., polyethylene glycol, Spacer 18 (Integrated DNA Technologies), and the like. Spacer 18 is an 18-atom hexa-ethyleneglycol spacer (shown below) and, in certain embodiments, between two and five units of Spacer 18 is linked to each end of the polynucleotide portion of a template localizing moiety.

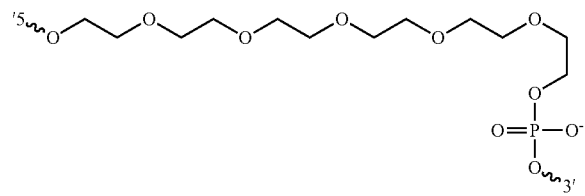

In yet further embodiments, a template localizing moiety comprises both one or more non-complementary polynucleotide portions and one or more synthetic polymer portions. Benefits from such hybrid structures are myriad and include less costly synthesis of the synthetic structural units and reduced potential for interference with a translocating polymerase. Further, the shape and/or stiffness of the portion of the template localizing moiety that bind, directly or indirectly, to the reaction region can be modified based upon the natural and/or synthetic structural unit composition. The biochemical characteristics of such structural units, as well as the chemical synthesis methods to link them, are well understood to those of ordinary skill in the art.

Further Details Regarding Coupling Template Localizing Moieties to Surfaces

Certain compositions of the invention optionally include a template localizing moiety that has been immobilized, e.g., on a planar surface, in a well, or in a single-molecular reaction region, e.g., a zero-mode waveguide (ZMW). In embodiments where the moiety comprises a protein, the protein is preferably immobilized in an orientation that preserves the protein's ability to bind/associate with a nucleic acid and, and in some embodiments form a complex with a sequencing enzyme. The immobilized template localizing moiety can fix a template nucleic acid to the surface and can thereby advantageously localize, e.g., a DNA sequencing reaction, e.g., a template-directed synthesis reaction, to a defined reaction site. As described elsewhere herein, such compositions can beneficially increase the lengths and accuracy of sequencing reads and lower fabrication costs and reagent use when used in, e.g., high-throughput single-molecule sequencing systems, and can allow the same template to be repeatedly processed under different reaction conditions, e.g., using different polymerases, buffers, labels, nucleotides (or analogs thereof), temperatures, divalent cations, and other reaction components, as well as using different illumination frequencies, power, intensities, and/or wavelengths. Further, a plurality of template localizing moieties can be immobilized on a support in a manner that provides optical resolvability between templates localized thereto, and such templates can be repeatedly processed under the same or different conditions. In certain embodiments, at least a portion of the multiple templates localized on such a support comprise identical and/or complementary nucleotide sequences relative to each other.

In some embodiments, the template localizing moiety can interact directly with a surface, as described below. Alternatively or in addition, a wide variety of linking chemistries are available for linking template localizing moieties, e.g., those described herein, to a wide variety of molecular, solid or semi-solid support elements. These chemistries can be performed in situ (i.e., in the reaction region in which the protein is to be immobilized) or prior to introduction of the template localizing moiety into the well or reaction region. It is impractical and unnecessary to describe all of the possible known linking chemistries for linking proteins to a solid support. It is expected that one of skill can easily select appropriate chemistries, depending on the intended application.

In one preferred embodiment, the surfaces to which a template localizing moiety is coupled comprise silicate elements (e.g., an array of ZMWs fabricated from glass or silicate compounds). A variety of silicon-based molecules appropriate for functionalizing surfaces are commercially available. See, for example, *Silicon Compounds Registry and Review*, United Chemical Technologies, Bristol, Pa.

Additionally, the art in this area is very well developed and those of skill will be able to choose an appropriate molecule for a given purpose. Appropriate molecules can be purchased commercially, synthesized de novo, or it can be formed by modifying an available molecule to produce one having the desired structure and/or characteristics.

The substrate linker attaches to the solid substrate through any of a variety of chemical bonds. For example, the linker is optionally attached to the solid substrate using carbon-carbon bonds, for example via substrates having (poly) trifluorochloroethylene surfaces, or siloxane bonds (using, for example, glass or silicon oxide as the solid substrate). Siloxane bonds with the surface of the substrate are formed in one embodiment via reactions of derivatization reagents bearing trichlorosilyl or trialkoxysilyl groups. The particular linking group is selected based upon, e.g., its hydrophilic/hydrophobic properties where presentation of an attached polymer in solution is desirable. Groups which are suitable for attachment to a linking group include amine, hydroxyl, thiol (e.g., in the case of gold surfaces), carboxylic acid, ester, amide, isocyanate and isothiocyanate. Preferred derivatizing groups include aminoalkyltrialkoxysilanes, hydroxyalkyltrialkoxysilanes, polyethyleneglycols, polyethyleneimine, polyacrylamide, polyvinylalcohol and combinations thereof.

By way of non-limiting example, the reactive groups on a number of siloxane functionalizing reagents can be converted to other useful functional groups:

1. Hydroxyalkyl siloxanes (Silylate surface, functionalize with diborane, and H2O2 to oxidize the alcohol);
    a. allyl trichlorosilane→→3-hydroxypropyl
    b. 7-oct-1-enyl trichlorchlorosilane→→8-hydroxyoctyl
2. Diol (dihydroxyalkyl) siloxanes (silylate surface and hydrolyze to diol)
    a. (glycidyl trimethoxysilane→→(2,3-dihydroxypropyloxy)propyl
3. Aminoalkyl siloxanes (amines requiring no intermediate functionalizing step)
    a. 3-aminopropyl trimethoxysilane→aminopropyl
4. Dimeric secondary aminoalkyl siloxanes
    a. bis(3-trimethoxysilylpropyl) amine→bis(silyloxylpropyl)amine.

See, for example, Leyden et al., Symposium on Silylated Surfaces, Gordon & Breach 1980; Arkles, Chemtech 7, 766 (1977); and Plueddemann, Silane Coupling Reagents, Plenum, N.Y., 1982. These examples are illustrative and do not limit the types of reactive group interconversions which are useful in conjunction with the present invention. Additional starting materials and reaction schemes will be apparent to those of skill in the art.

Template localizing moieties bearing a surface-exposed charge can then be coupled to a derivatized surface, e.g., planar surface, well, or single-molecule reaction region, e.g., ZMW. For example, the charged group can be a carboxylate, quaternary amine or protonated amine that is a component of, e.g., an amino acid that has a charged or potentially charged side chain. The amino acids can be either those having a structure which occurs naturally or they can be of unnatural structure (i.e., synthetic). Useful naturally occurring amino acids include: arginine, lysine, aspartic acid and glutamic acid. Surfaces utilizing a combination of these amino acids can be of use in the present invention. Further, peptides comprising one or more residues having a charged or potentially charged side chain are useful coating components and they can be synthesized utilizing arginine, lysine, aspartic acid, glutamic acid and combinations thereof. Useful unnatural amino acids are commercially available or can be synthesized utilizing art-recognized methodologies, such as available systems of orthogonal elements. In those embodiments in which an amino acid moiety having an acidic or basic side chain is used, these moieties can be attached to a surface bearing a reactive group through standard peptide synthesis methodologies or easily accessible variations thereof. See, for example, Jones, Amino Acid and Peptide Synthesis, Oxford University Press, Oxford, 1992.

Linking groups can also be placed on surfaces to which a template localizing moiety is to be immobilized. Linking groups of use in the present invention can have a range of structures, substituents and substitution patterns. They can, for example be derivatized with nitrogen, oxygen and/or sulfur containing groups which are pendent from, or integral to, the linker group backbone. Examples include, polyethers, polyacids (polyacrylic acid, polylactic acid), polyols (e.g., glycerol,), polyamines (e.g., spermine, spermidine) and molecules having more than one nitrogen, oxygen and/or sulfur moiety (e.g., 1,3-diamino-2-propanol, taurine).

In some aspects, the coupling chemistries for coupling a template localizing moiety to a surface of interest can be light-controllable, i.e., utilize photo-reactive chemistries. The use of photo-reactive chemistries and masking strategies to activate coupling of molecules, e.g., template localizing moieties, to substrates, as well as other photo-reactive chemistries is generally known (e.g., for semi-conductor chip fabrication and for coupling bio-polymers to solid phase materials). Among a wide variety of protecting groups which are useful are nitroveratryl (NVOC)-methylnitroveratryl (Menvoc), allyloxycarbonyl (ALLOC), fluorenylmethoxycarbonyl (FMOC), -methylnitro-piperonyloxycarbonyl (MeNPOC), —NH-FMOC groups, t-butyl esters, t-butyl ethers, and the like. Various exemplary protecting groups (including both photo-cleavable and non-photo-cleavable groups) are described in, for example, Atherton et al., (1989) Solid Phase Peptide Synthesis, IRL Press, and Greene, et al. (1991) Protective Groups In Organic Chemistry, 2nd Ed., John Wiley & Sons, New York, N.Y. The use of these and other photo-cleavable linking groups for nucleic acid and peptide synthesis on solid supports is a well-established methodology.

Devices, methods and systems that incorporate functionalized regions into the walls of a ZMW, e.g., by incorporating an annular gold ring into the walls of the ZMW, are described, e.g., in Foquet et al. SUBSTRATES AND METHODS FOR SELECTIVE IMMOBILIZATION OF ACTIVE MOLECULES (U.S. Ser. No. 60/905,786, filed Mar. 7, 2007 and U.S. Patent Publication No. 20080220537), incorporated herein by reference in their entireties for all purposes.

Template localizing moieties can include appropriate functionalities for linking to the relevant array surface. For example, thiol chemistries can be used to link, e.g., a template localizing moiety to, e.g., a planar surface, a well, or a single molecule reaction region. Template localizing moieties can include linking groups, e.g., one or more biotin tags, SNAP tags, CLIP tags, or a combination thereof, all of which are known in the art and commercially available. For example, a template localizing moiety can comprise a fusion protein between a sliding clamp protein and a biotin tag that facilitates immobilization of the sliding clamp protein by binding to streptavidin on the surface. Template localizing moieties that comprise recombinantly expressed proteins can also include unnatural amino acids with any of a variety of linking chemistries, e.g., when expressed in a host cell that includes orthogonal elements that permit site-specific expression of the unnatural amino acid. Systems of orthogonal elements that can be used to incorporate unnatural amino acids, including amino acids with reactive groups, are described in Wang, et al. (2006) "Expanding the genetic code," *Annu Rev Biophys Biomolec Struct* 35: 225-249; Wang and Schultz (2005) "Expanding the Genetic Code," *Angewandte Chemie Int. Ed.* 44(1):34-66; Xi; et al. (2005) "An expanding genetic code." Methods 36: 227-38; and Xie, et al. (2006) "A chemical toolkit for proteins: an expanded genetic code." *Nat Rev Mol Cell Biol* 7: 775-82.

The site-specific incorporation of an amino acid that comprises a reactive/linking group can be used to specifically orient, e.g., a template localizing moiety that comprises a protein, relative to a well or single molecule reaction region. Most preferably, such a protein is immobilized in, e.g., a ZMW, in an orientation that permits the protein to retain its activity, e.g., its ability to bind/associate with a template nucleic acid and, e.g., form a complex with a polymerase. For example, the well or reaction region can include a specific functionalized region (e.g., a gold band, as discussed above) that can be coupled to a specific portion of the template localizing moiety. Additional useful strategies for coupling proteins to surfaces are detailed in, e.g., WO 2007/076057 PROTEIN ENGINEERING STRATEGIES TO OPTIMIZE ACTIVITY OF SURFACE ATTACHED PROTEINS by Hanzel et al.

Sequencing Enzymes

The invention provides compositions that include a localizing moiety on, e.g., a planar surface, a well, or a single molecule reaction region. Such compositions can be useful in fixing a template nucleic acid to the surface, e.g., by topologically encircling the template, and localizing the template to, e.g., a defined reaction region, e.g., a single-molecule reaction volume. A template localizing moiety can comprise a polymer, e.g., a protein other than a polymerase, and in particular other than a polymerase used as a sequencing enzyme, e.g., to perform template-directed sequencing-by-synthesis. In certain embodiments of the invention, a sequencing enzyme can be engineered to covalently bind to a template localizing moiety, e.g., via a polymerase's C-terminal end (see FIG. 4 and corresponding description). Optionally, a sequencing enzyme can be temporarily tethered to a template localizing moiety via, e.g., a reversibly cleavable linker, e.g., a linker that can reform with a new sequencing enzyme. As noted elsewhere herein, polymerase enzymes can optionally be immobilized in certain embodiments of the methods and compositions provided herein. Methods for immobilization of peptides, such as enzymes, are known and widely used in the art. For example, specific methods are provided in U.S. Pat. Nos. 5,723,584, 5,874, 239, and 5,932,433, the disclosures of which are incorporated herein by reference in their entireties for all purposes.

In certain preferred embodiments, the template localizing moiety is configured to non-covalently associate with a sequencing enzyme, or to associate exclusively with the template and not with the sequencing enzyme. In certain embodiments, a sequencing enzyme included in the compositions can process a portion of at least one strand of the fixed template and exchange with a second sequencing enzyme, e.g., without terminating the sequencing reaction. The exchange of sequencing enzymes during nucleic acid sequencing reactions can be particularly beneficial in, e.g., single-molecule template-directed synthesis reactions, e.g., performed in a ZMW, where a polymerase's processivity, accuracy, and polymerase activity can decrease over time or can produce a bias for a certain type of error in the resulting sequencing reads. Such an exchange can occur during the course of a sequencing reaction, or after completion of a sequencing reaction, e.g., in a subsequent sequencing reaction. In one example, a DNA polymerase that has sustained photodamage can exchange with a non-photodamaged DNA polymerase without disrupting the sequencing read (see FIG. 3 and corresponding description), thus maintaining the accuracy with which the correct nucleotide is incorporated into a newly synthesized nucleic acid and/or increasing sequence throughput. In other examples, a first polymerase that displays a bias for introducing insertion errors is used to produce one or more reads of a template nucleic acid, and is then exchanged for a second polymerase that displays a bias for introducing deletion errors. Both polymerases may be present in a single reaction mixture, or the exchange can involve removing a reaction mixture comprising the first polymerase and introducing a reaction mixture comprising the second polymerase. The data generated using the first polymerase is expected to have a bias for a first type of error, e.g., insertion errors, and the data generated using the second polymerase is expected to have a bias for a second type of error, e.g., deletion errors. As such, the data generated using the second polymerase can be used to identify and correct the errors (e.g., insertions) in the data generated using the first polymerase; and the data generated using the first polymerase can be used to identify and correct the errors (e.g., deletions) in the data generated using the second polymerase, resulting in a final consensus sequence read for the template nucleic acid that is more accurate than any single sequencing read by either polymerase.

The exchange of polymerases is also beneficial where different types of polymerases are present in a reaction mixture, e.g., as in the JumpStart RED HT RT-PCR kit (Sigma-Aldrich®). Different types of polymerases often have different characteristics, including but not limited to processivity, specificity, fidelity, rate of incorporation, rate of translocation, retention time of a nucleotide in the active site during incorporation, pulse characteristics (further described elsewhere herein), and "error profiles" (also termed "error modes"), which includes the propensity for sequencing data from a given polymerase to have certain kinds of errors, such as deletions, insertions, substitutions, branching, etc. As such, the error profile of a polymerase is sometimes referred to as the accuracy or fidelity of the enzyme. Given that different polymerase enzymes can have different error profiles, multiple polymerases used to sequence a single template nucleic acid can be chosen to have "complementary" error profiles such that the error types that characterize sequence data from a first polymerase will not characterize the sequence data generated using the second polymerase, and vice versa. For any position in the resulting reads for which there is a difference between the reads generated by the first and second polymerases, knowledge of the error profiles of each will inform as to which base call is correct for that position. For example, if one polymerase has a relatively high deletion frequency, and a second polymerase has a relatively low deletion frequency, deletions present in a read generated by the first polymerase that are absent in a read generated by the second polymerase will generally be understood to be a polymerase artifact and not reflective of the actual sequence of the template nucleic acid. As such, in some embodiments, a set of two or more polymerases having complementary error profiles are chosen for use in a single sequencing reaction, and the complementary error profiles are exploited to produce a consensus sequence read for the target nucleic acid. The different polymerases can be present in a single reaction mixture, or multiple reaction mixtures comprising different types of polymerases can be sequentially introduced to a template to be sequenced.

Characteristics of polymerase activity are also impacted by reaction conditions and components, including but not limited to pH, buffer composition, selection and concentration of divalent cations, temperature, using different illumination frequencies, power, intensities, and/or wavelengths, type of nucleotide or nucleotide analog, type of labels and/or linking groups, and even template sequence. As noted above, the behavior of a polymerase enzyme at a particular position on a template is influenced by the sequence context within which the particular position is found, and this influence can be modulated by varying other aspects of the reaction conditions. As such, the error profile of a given polymerase includes its sensitivity and response to various types of sequence contexts in a template molecule, e.g., under one or more reaction conditions. For example, a polymerase can have a propensity to produce sequence reads having insertions in highly repetitive regions, but not in low-repeat regions, or to incorporate noncognate nucleotides at a particular position within a sequence context. As such, certain polymerases have error profiles that are dependent on sequence context, exhibiting different error frequencies under different sequence context conditions. Since different polymerases have different sensitivities and responses to sequence context, using a combination of polymerases provides sequence reads with differing dependencies on sequence context. Further, using varying reaction conditions, even with a single type of polymerase enzyme, can generate sequence data that is more or less sensitive to a given sequence context. In certain embodiments, multiple different types of polymerases are used at multiple different reaction conditions. As above, for positions in the resulting reads for which there is a difference between the reads generated by a first polymerase having a first sequence context response and second polymerases having a second sequence context response, knowledge of the error profiles (including the sequence context sensitivity) of each, as well as the related reaction condition effects, will inform as to which base calls are correct for those positions.

In certain embodiments, more than one polymerase may be present in a template-directed sequencing reaction in which one or more lesions may be present on the template nucleic acid. For example, "bypass polymerases" have been discovered in both prokaryotes and eukaryotes, most of which belong to the Y-family of polymerases and/or are considered to be repair polymerases. In contrast to replicative polymerases, they operate at low speed, low fidelity, and low processivity. However, because their active sites adopt a more open configuration than replicative polymerases they are less stringent and can accommodate altered bases in their active sites. For more information on bypass polymerases, see, e.g., Cordonnier, et al. (1999) Mol Cell Biol 19(3): 2206-11; Friedberg, et al. (2005) Nat Rev Mol Cell Biol 6(12):943-53; Holmquist, et al. (2002) Mutat Res 510(1-2): 1-7; Lehmann, A. R. (2002) Mutat Res 509(1-2):23-34; Lehmann, A. R. (2006) Exp Cell Res 312(14):2673-6; Masutani, et al. (1999) Nature 399(6737):700-4; and Ohmori, et al. (2001) Mol Cell 8(1):7-8, the disclosures of which are incorporated herein by reference in their entireties for all purposes. Certain of these polymerases can bypass lesions in a nucleic acid template and carry out "translesion synthesis" or TLS. As such, DNA replication in the presence of such lesions was found to require multiple polymerases and the "polymerase switch model" was developed (see, e.g., Friedberg, et al. (2005) Nat Rev Mol Cell Biol 6(12): 943-53; Kannouche, et al. (2004) Cell Cycle 3(8):1011-3; Kannouche, et al. (2004) Mol Cell 14(4):491-500; and Lehmann, et al. (2007) DNA Repair (Amst) 6(7):891-9, all of which are incorporated herein by reference in their entireties for all purposes). In brief, the polymerase switch model is model for lesion bypass during replication that involves replacement of a replicative polymerase with a bypass polymerase at a lesion, synthesis of the nascent strand by the bypass polymerase until past the lesion, and subsequent replacement of the bypass polymerase with the more processive, higher fidelity replicative polymerase for continued replication past the lesion. For example, during the course of a reaction in which a replicative polymerase encounters and is blocked by a lesion in a template nucleic acid, the replicative polymerase is replaced by a bypass polymerase at the site of the lesion, and the bypass polymerase synthesizes a segment of the nascent strand that is capable of base-pairing with the damaged base, and may further include one or more bases prior to and/or past the site of the lesion in a process called "translesion synthesis." The limited processivity of the bypass polymerase causes it to dissociate and be replaced by the replicative polymerase following translesion synthesis. The replicative polymerase continues to synthesize the nascent strand until another blocking lesion is encountered in the template, at which point it is once again replaced by a bypass polymerase for translesion synthesis. (See, e.g., Friedberg, et al. (2005) Nat Rev Mol Cell Biol 6(12):943-53; and Kannouche, et al. (2004) Mol Cell 14(4):491-500, incorporated herein by reference above.) The process continues until the template has been fully and/or iteratively processed, or the reaction is terminated, e.g., by the investigator. One particular advantage of the polymerase switch method of template-dependent sequencing is that is it tolerant of most types of lesions in the template nucleic acid. As such the damaged template can be sequenced through a lesion, thereby allowing reinitiation of synthesis downstream of the lesion and increasing read lengths on lesion-containing templates.

Various different bypass polymerases known to those of ordinary skill in the art can be used with the methods and compositions provided herein, include prokaryotic polymerases (e.g., DNA polymerase IV, polymerase V, Dpo4, Dbh, and UmuC) and eukaryotic polymerases (e.g., DNA polymerase DNA polymerase I, DNA polymerase K, and Rev 1). In eukaryotes, multiple bypass polymerases participate in translesion synthesis, and a processivity factor, proliferating cell nuclear antigen ("PCNA"), is also required and can be included in a sequencing reaction.

Monitoring reactions in which a template comprises damage or other modifications (collectively "lesions") generates data that can be statistically analyzed to determine the number and locations of lesions in the template, and can potentially identify the type of lesion. (See, e.g., U.S. 20100221716, incorporated herein by reference in its entirety for all purposes.) Since the portion of the nascent strand corresponding to the site of the lesion in the template is synthesized by a bypass polymerase, the sequence reads generated therefrom are expected to be less reliable than those generated from regions of the nascent strand synthesized by the replicative polymerase. As such, redundancy in the sequencing reaction is a preferred means of generating complete and accurate sequence reads.

Redundancy can be achieved in various ways, including carrying out multiple repeated sequencing reactions on a single template molecule, or by multiple sequencing reactions using multiple copies of the same original template, e.g., in an array format, e.g., a ZMW array. These reactions can be performed with the same or different polymerases in the same or different reaction mixtures under the same or different reaction conditions. They may be performed with the template immobilized or otherwise localized, with the polymerase immobilized or otherwise localized, or with both confined to a given reaction region. In some embodiments in which a lesion is unlikely to occur in all the copies of a given template, the sequence data generated in multiple reactions using multiple different copies of the template can be combined and subjected to statistical analysis to determine a consensus sequence for the template. In this way, the sequence data generated by processing the template with a lower fidelity (e.g., "bypass") polymerase can be supplemented and/or corrected with sequence data generated by processing the same template with a higher fidelity (e.g., "replicative") polymerase. Alternatively or additionally, a template can be subjected to repeated sequencing reactions to generate redundant sequence information that can be analyzed to more thoroughly characterize the lesion(s) present in the template, e.g., by using a single-stranded circular template nucleic acid immobilized at a reaction site by various methods described elsewhere herein. Such repeated sequencing reactions can be identical, or may differ in various aspects, e.g., type of polymerase, nucleotides (or analogs thereof), labels, or divalent cation(s); temperature; pH; illumination frequency, power, intensity, and/or wavelength, etc. Methods for template damage detection and bypass are further described in U.S. Ser. No. 61/186,661, filed Jun. 12, 2009, and U.S. Patent Publication No. 20100221716, both of which are incorporated herein by reference in their entireties for all purposes. Further, the templates used may comprise identical nucleotide sequences of interest, but not be entirely identical, such as when the templates are products of random fragmentation or amplification. The redundant sequence information is generated from the portions of the templates that comprise the nucleotide sequences of interest common to all or a portion of them.

As noted above, redundancy is also achieved through analysis of sequence reads of the same region of a template nucleic acid by different types of polymerases. In some embodiments, more than one reaction mixture is exposed to the same template or set of templates. A set of templates can comprise copies of a template, complements of a template, templates that are partially identical or complementary, and/or templates that are not identical or complementary. The sequence data generated will serve to identify a particular template molecule. Each reaction mixture has a different polymerase composition. For example, each can have a different single type of polymerase or a unique composition of different polymerases. Unique compositions can contain different types of polymerases, different amounts of the same types of polymerases, or a combination thereof. Typically the polymerases are mixed prior to addition of a reaction mixture to a template or set of templates, but they can also be added separately, e.g., simultaneously or sequentially, to the template(s) without complete replacement of the reaction mixture. In some embodiments, known characteristics of the polymerases are used to identify which in a mixture of polymerases produces a given sequencing read from a given template, e.g., where a mixture of polymerases is present on an array comprising multiple localized templates. Alternatively, the polymerases can be differentially labeled by methods known in the art to allow identification of a polymerase as it processes a given template molecule. In addition, generation of the replicate or redundant sequence information can be performed under different reaction conditions, e.g., temperature, divalent cation, pH, illumination characteristics, reaction mixture, choice of nucleotide analog and/or label, etc. For example, in certain embodiments reaction conditions are chosen that are known to promote the activity of one or more polymerases present in the reaction. In other embodiments, reaction conditions that have a known effect on the error profile of one or more polymerases in the reaction mixture are chosen.

DNA polymerases are sometimes classified into six main groups based upon various phylogenetic relationships, e.g., with *E. coli* Pol I (class A), *E. coli* Pol II (class B), *E. coli* Pol III (class C), Euryarchaeotic Poi II (class D), human Pol beta (class X), and *E. coli* UmuC/DinB and eukaryotic RAD30/xeroderma pigmentosum variant (class Y). For a review of recent nomenclature, see, e.g., Burgers et al. (2001) "Eukaryotic DNA polymerases: proposal for a revised nomenclature" *J Biol Chem* 276: 43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1): reviews 3002.1-3002.4; and Steitz (1999) "DNA polymerases: structural diversity and common mechanisms" J Biol Chem 274:17395-17398. The basic mechanisms of action for many polymerases have been determined, as have their different characteristics, such as processivity, activities using different template nucleic acids, fidelities, rates, retention times, error profiles (e.g., types and frequencies of different types of errors), incorporation/translocation rates, preferred reaction conditions, behavior under non-preferred conditions, etc. The sequences of literally hundreds of polymerases are publicly available, and the crystal structures for many of these have been determined, or can be inferred based upon similarity to solved crystal structures for homologous polymerases. For example, the crystal structure of Φ29, a preferred type of parental enzyme to be modified according to the invention, is available. (See, e.g., Berman et al. (2007) EMBO J 26:3494-3505, Kamtekar et al. (2006) EMBO J 25:1335-1343, and Kamtekar et al. (2004) Mol Cell 16:609-618.)

Structure/function analysis has revealed that most DNA polymerases comprise a separate exonuclease domain. Many DNA polymerase enzymes have been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. DNA polymerases have also been modified to confer improvements in specificity, processivity, and improved retention time of labeled nucleotides in polymerase-DNA-nucleotide complexes (e.g., WO 2007/076057 POLYMERASES FOR NUCLEOTIDE ANALOG INCORPORATION by Hanzel et al., and PCT/US2007/022459 POLYMERASE ENZYMES AND REAGENTS FOR ENHANCED NUCLEIC ACID SEQUENCING by Rank et al.), to improve surface-immobilized enzyme activities (e.g., WO 2007/075987 ACTIVE SURFACE COUPLED POLYMERASES by Hanzel et al., and WO 2007/076057 PROTEIN ENGINEERING STRATEGIES TO OPTIMIZE ACTIVITY OF SURFACE ATTACHED PROTEINS by Hanzel et al.), to increase closed complex stability and/or reduce branching rate (e.g., 61/072,645 GENERATION OF POLYMERASES WITH IMPROVED CLOSED COMPLEX STABILITY AND DECREASED BRANCHING RATE by Clark, et al.), and to reduce susceptibility to photodamage (e.g., 61/072,643 ENZYMES RESISTANT TO PHOTODAMAGE by Bjornson, et al.). Any of these available polymerases can be included with the surface-immobilized template localizing moiety in the compositions, methods or systems of the invention to, e.g., improve the accuracy of sequencing data and/or increase the read lengths of sequencing reactions. For example, a polymerase having high processivity but a higher-than-desired indel error profile can be used to initially sequence a template nucleic acid, e.g., to generate a sequence scaffold from multiple sequence reads from the same template. Subsequently, a less processive but highly accurate polymerase can be used to generate a highly accurate read to be aligned with the scaffold and used to identify and correct any indels introduced into the sequencing reads by the less accurate polymerase. In this way, high-fold coverage can be combined with high accuracy using two enzymes with differing error profiles. Similarly, polymerases can be combined that have differing incidences of substitution errors, more or less noncognate sampling, differing residence times during which a nucleotide is held in the binding pocket prior to incorporation, differing translocation rates, and the like. Analysis of sequence reads from polymerases having known error profiles can take those profiles into account and produce a final consensus sequence read that is corrected for the various different types of errors introduced by the different polymerases. One particular example is provided above with regards to the use of bypass polymerases in combination with other polymerases.

Many such polymerases are available, e.g., for use in sequencing, labeling and amplification technologies. For example, Human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. Φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ Φ29 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot)com provides comparisons of many different commercially available polymerases.

DNA polymerases that are preferably included in the methods, compositions, and/or systems of the invention, e.g., to increase the read lengths of sequencing reactions, include Taq polymerases, exonuclease-deficient Taq polymerases, E. coli DNA Polymerase I, Klenow fragment, reverse transcriptases, Φ29-related polymerases including wild-type Φ29 polymerase and derivatives of such polymerases such as exonuclease-deficient forms, T7 DNA polymerase, T5 DNA polymerase, an RB69 polymerase, etc. Further, in certain preferred embodiments, polymerases that are preferably included in the methods, compositions, and/or systems of the invention are capable of strand displacement. A variety of strand-displacing polymerase enzymes are readily available, including, for example, Φ29 polymerase and Φ29-type polymerases (See, e.g., U.S. Pat. Nos. 5,001,050, 5,576,204, the full disclosures of which are incorporated herein by reference in their entirety for all purposes), Bst polymerase (available from New England Biolabs), as well as those polymerases described in commonly owned International Patent Application Nos. WO 2007/075987, WO 2007/075873, WO 2007/076057 the full disclosures of which are incorporated herein by reference in their entirety for all purposes.

In one aspect, a polymerase (e.g., singly or in a set of different types of polymerases) that is included with an immobilized template localizing moiety in the methods, compositions and/or systems of the invention is a Φ29-type DNA polymerase. For example, the modified, recombinant DNA polymerase can be homologous to a wild-type or exonuclease-deficient Φ29 DNA polymerase, e.g., as described in U.S. Pat. Nos. 5,001,050, 5,198,543, or 5,576,204. Alternately, DNA polymerase of the methods, systems, and/or compositions can be homologous to other Φ29-type DNA polymerases, such as B103, GA-1, PZA, Φ15, BS32, M2Y, Nf, G1, Cp-1, PRD1, PZE, SF5, Cp-5, Cp-7, PR4, PR5, PR722, L17, Φ21, or the like. For nomenclature, see also, Meijer et al. (2001) "Φ29 Family of Phages" Microbiology and Molecular Biology Reviews, 65(2): 261-287.

In addition to wild-type polymerases, chimeric polymerases made from a mosaic of different sources can be included in the compositions and methods described herein. For example, Φ29 polymerases made taking sequences from more than one parental polymerase into account can be used as a starting point for mutation to produce the polymerases of the invention. This can done, e.g., using consideration of similarity regions between the polymerases to define consensus sequences that are used in the chimera, or using gene shuffling technologies in which multiple Φ29-related polymerases are randomly or semi-randomly shuffled via available gene shuffling techniques (e.g., via "family gene shuffling"; see Crameri et al (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mal. Biol. 330:287-296). In these methods, the recombination points can be predetermined such that the gene fragments assemble in the correct order. However, the combinations, e.g., chimeras, can be formed at random. Using the methods described above, a chimeric polymerase, e.g., comprising segments of a 13103 polymerase, a GA-1 polymerase, a PZA polymerase, a Φ15 polymerase, a BS32 polymerase, a M2Y polymerase, an Nf polymerase, a G1 polymerase, a Cp-1 polymerase, a PRD1 polymerase, a PZE polymerase, an SF5 polymerase, a Cp-5 polymerase, a Cp-7 polymerase, a PR4 polymerase, a PR5 polymerase, a PR722 polymerase, an L17 polymerase, and/or an F21 polymerase, can be generated for use with template localizing moieties in compositions and methods provided by the invention.

As described above, template localization moieties are also useful in exonuclease sequencing applications. Briefly, exonuclease sequencing determines the sequence of a nucleic acid by degrading the nucleic acid unilaterally from a first end with an exonuclease to sequentially release individual nucleotides. Each of the sequentially released nucleotides is identified, e.g., by mass spectrometry, and the sequence of the nucleic acid is determined from the sequence of released nucleotides. Various exonucleases known in the art are useful for exonuclease sequencing, including but not limited to T7 exonuclease, ExoIII, ExoVII, mung bean nuclease, lambda exonuclease, and the exonuclease activity of various polymerases (e.g., Klenow, polI, Taq polymerase, and T4 polymerase). Sequencing by exonuclease degradation is described further, e.g., in U.S. Pat. Nos. 5,622,824 and 5,516,633; and in international application no. PCT/US1994/003416. A template nucleic acid immobilized by a template localizing moiety can be subjected to degradation by an exonuclease and the resulting free nucleotides can be detected by methods known in the art, including mass spectrometry, optical detection of fluorescent or luminescent labels on the released nucleotides, passage through a nanopore, etc. In certain embodiments, a combination of exonucleases having differing characteristics are used on multiple copies and/or complementary copies of a given template nucleic acid. In some embodiments, such experiments are performed under differing conditions known to affect the activity of the exonuclease enzyme(s). In some embodiments, the template is a long, concatemeric nucleic acid and exchange of the exonuclease enzyme is performed such that a first portion of the template is sequenced by a first exonuclease and a second portion of the template is sequenced by a second exonuclease.

In further embodiments, a combination of an exonuclease and one or more polymerases can be used to determine the sequence of a template nucleic acid, e.g., by subjecting a single-stranded circular template nucleic acid to rolling circle amplification by the polymerase, degrading the resulting nascent strand with an exonuclease, and detecting the release of nucleotides. This method provides an added benefit by allowing repeated sequencing of the circular template since the exonuclease acts only on the nascent strand, which is a concatemeric complement of the circular template. In related embodiments, a template can be first sequenced by template-directed nascent strand synthesis, and subsequently sequenced by nucleolytic degradation. Reaction conditions and components, including use of multiple different polymerases and/or exonucleases, can also be varied as described at length above.

Further Details Regarding Nucleic Acid Amplification and Sequencing

Certain compositions of the invention include surface-immobilized template localizing moieties in combination with one or more sequencing enzymes, e.g., for sequencing a template nucleic acid. In certain embodiments, a sequencing enzyme can associate with the template localizing moiety in a non-covalent manner or bind the moiety via a reversibly cleavable linker, e.g., a linker that can reform with a new sequencing enzyme. In other embodiments, the sequencing enzyme can be non-covalently bound to other than the template localizing moiety, e.g., a surface at the reaction region. Thus, the template can advantageously be sequenced in a manner that permits the exchange of a first (e.g., inactive, photodamaged, mismatch error-prone, insertion error-prone, deletion error-prone, non-processive, etc.) sequencing enzyme, with a second (e.g., active, non-photodamaged, differently error-prone, processive, etc.) sequencing enzyme, e.g., without terminating the sequencing reaction. For example, during template-dependent synthesis of a nascent nucleic acid, an inactive polymerase can be replaced by an active polymerase, allowing stalled nascent strand synthesis to reinitiate; or a first polymerase having a first error profile can be replaced by a second polymerase having a second error profile. Further the localized template can be repeatedly processed under a variety of conditions apart from varying the type of polymerase(s) present. For example, various conditions that can be modified include temperature, pH, buffer, divalent cation, types of labels, nucleotides or other reaction components, illumination type, and the like, which can affect the sequencing reads generated, e.g., by altering the error profile of the polymerase(s). In certain embodiments, the sequencing enzyme is non-covalently attached at the reaction region, e.g., to the template localizing moiety or a surface, via a reversibly cleavable linker, or more preferably a photocleavable linker, as further described elsewhere herein. In other embodiments of the sequencing reactions provided by the invention, a sequencing enzyme can be covalently bound in the reaction region, e.g., to a surface or to the immobilized template localizing moiety, e.g., at the C-terminal end of a polymerase (see, e.g., FIG. 4).

Embodiments comprising unlocalized templates are also contemplated. In yet further embodiments, one or more sequencing enzymes is bound to a surface, e.g., in an arrayed format. For example, an amplified template molecule, i.e., multiple copies of the same template, can be applied to a surface having multiple different types of polymerases bound thereto at known or determinable locations. The identity of a polymerase can be accomplished in various ways, including those disclosed herein, e.g., by detection of a label specific for a particular type of polymerase or through analysis of a sequencing read produced by the polymerase. Algorithms for polymerase identification are described elsewhere herein. If a polymerase stalls or otherwise releases a template, the template is free to bind to another polymerase of the same or different type and continue to serve as a template for nascent strand synthesis by the other polymerase. Further, a linear template completely sequenced by one polymerase and thereby rendered double-stranded can be subjected to a treatment to remove one of the strands (e.g., a nuclease treatment with, e.g., a dsDNA-dependent ssDNA exonuclease). The resulting single-stranded template (which may contain sequence from the original template or the complementary nascent strand) is subsequently resequenced by the same or another polymerase.

The template nucleic can be a linear or circular molecule, and in certain applications, is desirably a circular template (e.g., for rolling circle replication or for sequencing of circular templates), as shown in FIGS. 2 and 3. Optionally, the composition can be present in an automated nucleic acid synthesis and/or sequencing system. A template nucleic acid can be double-stranded and/or single-stranded, and can comprise DNA, RNA, analogs and/or derivatives thereof, and combinations of the same. A template nucleic acid can comprise chemical or other modifications (e.g., labels, nucleotide analogs or derivatives, lesions, non-standard nucleotides, methylated nucleotides, synthetic nucleotides, etc.). Certain preferred templates are provided in U.S. Patent Publication No. 20090280538, which is incorporated herein by reference in its entirety for all purposes.

For template-directed sequencing-by-synthesis reactions, a replication initiating moiety in the reaction mixture can be a standard complementary oligonucleotide primer, or, alternatively, a component of the template, e.g., the template can be a self-priming single-stranded DNA (e.g., with a hairpin structure at the 3' end), a nicked or gapped double-stranded DNA, or the like. Such an oligonucleotide primer can comprise native or modified nucleotides, or derivatives, analogs, and/or combinations thereof. Similarly, a terminal protein can serve as an initiating moiety. At least one nucleotide analogue can be incorporated into the DNA.

Additional details of and methods for sequencing by incorporation methods are known in the art, e.g., in U.S. Pat. Nos. 6,787,308, 6,255,083, 5,547,839, and 6,210,896; U.S.S.N. 2004/0152119, 2003/0096253, 2004/0224319, 2004/0048300, 2003/0190647, 2003/0215862, 2009/0298075, 2010/0081143, and 2010/0075327; and international application nos. WO/1996/027025, WO/1999/005315, and WO/1991/006678, all of which are incorporated herein by reference in their entireties for all purposes.

The compositions of the invention can localize the incorporation of labeled nucleotides/analogs to a defined reaction region, regardless of which components of the sequencing complex are immobilized or otherwise localized at the reaction region. This can be of particularly beneficial use in a variety of different nucleic acid analyses, including real-time monitoring of DNA polymerization and degradation, e.g., at the single molecule level. For example, a fluorescent or chemiluminescent label can be incorporated, or more preferably, can be released during incorporation of the analogue into a nascent nucleic acid strand. In preferred embodiments, the label is released such that the nascent strand produced does not comprise the label. This is distinct from methods using labeled nucleotides that are detected after they are incorporated into the nascent strand, such as so-called "flush-and-scan" methods. Analogue incorporation can be monitored in real-time by monitoring label release during incorporation of the analogue by a polymerase that can exchange with a second polymerase in the reaction mixture, e.g., without terminating the sequence read or to produce a further sequence read from the same template. The portion of a nucleotide analogue that is incorporated, e.g., into the copied nucleic acid can be the same as a natural nucleotide, or can include features of the analogue that differ from a natural nucleotide. However, in especially preferred embodiments, the nascent nucleic acid strand produced is entirely native, i.e., has no remnants of the labeling group or other changes relative to a natural polynucleotide. Alternatively or additionally, other methods for detection of nucleotide incorporation may be employed, e.g., luciferase-mediated detection of released pyrophosphate. A further advantage to embodiments in which the template nucleic acid is not degraded, the same template molecule can be repeatedly sequenced to generate redundant sequence information. In embodiments comprising localization of the template, redundant sequence information for a single template molecule can be generated at a single reaction region. Further, the replicative sequencing operations can be performed under different reaction conditions, and the results can therefore be analyzed to determine the effects of the different reaction conditions on the reaction. In some embodiments, the reaction conditions are altered in ways that have predictable effects on the reaction such that each condition can provide a particular type of result, e.g., high fidelity, high processivity, fewer of a given type of error, higher enzyme rate of incorporation or translocation, longer retention time of nucleotide or nucleotide analog in the active site prior to incorporation, more or less stringent specificity, preferred pulse characteristics, etc. For example the chemistry rate is sensitive to the pH in the range of 6.5 to 9.0. In general the rate of the chemical reaction will appear to be faster at higher pH. This has the effect of reducing the observed pulse width (which increases the deletion error profile, e.g., because some pulses may be too brief to be detected) but decreasing the branching fraction, which means there's a decrease in the likelihood of detecting two or more pulses from a single labeled nucleotide analog during a single incorporation event. Additional examples of the effects of reaction conditions on polymerase activity can be found in, e.g., U.S. Patent Publication No. 2010/0047802, incorporated herein by reference in its entirety for all purposes.

In general, label incorporation or release can be used to indicate the presence and composition of a growing nucleic acid strand, e.g., providing evidence of template-directed synthesis/amplification and/or sequence of the template. Signaling from the incorporation can be the result of detecting labeling groups that are liberated from the incorporated analogue, e.g., in a solid phase assay, or can arise upon the incorporation reaction. For example, in the case of FRET labels where a bound label is quenched and a free label is not, release of a label group from the incorporated analogue can give rise to a fluorescent signal. Alternatively, polymerases present in a sequencing reaction mixture, e.g., that can be exchanged during the sequencing reaction, may be labeled with one member of a FRET pair proximal to the active site, and incorporation of an analogue bearing the other member will allow energy transfer upon incorporation. The use of enzyme bound FRET components in nucleic acid sequencing applications is described, e.g., in U.S. Patent Application Publication No. 2003/0044781, incorporated herein by reference in its entirety for all purposes.

In one example reaction of interest, a surface-bound template localizing moiety can be used to isolate a nucleic acid polymerization reaction within an extremely small observation volume that effectively results in observation of individual template-directed synthesis reactions. As a result, the incorporation event provides observation of an incorporating nucleotide analogue that is readily distinguishable from non-incorporated nucleotide analogues. That is, when a polymerase incorporates complementary, fluorescently labeled nucleotides into the nucleic acid strand that is being synthesized, the enzyme holds each nucleotide within the detection volume for tens of milliseconds, e.g., orders of magnitude longer than the amount of time it takes an unincorporated nucleotide to diffuse in and out of the detection volume. As described above, the polymerase can be exchanged with a second polymerase in the reaction mixture without terminating the sequence of incorporation events and/or the reaction can be repeated to generate multiple nucleotide sequence reads for the same template nucleic acid. In further embodiments, the polymerase can be immobilized at the reaction site, e.g., through an interaction with the template localizing moiety or a surface at the reaction site. In yet further embodiments, the polymerase is immobilized and the template nucleic acid is not.

In a preferred aspect, such small observation volumes are provided by immobilizing the template localizing moiety within an optical confinement, such as a zero-mode waveguide (ZMW). For a description of ZMWs and their application in single molecule analyses, and particularly nucleic acid sequencing, see, e.g., U.S. Patent Application Publication No. 2003/0044781, and U.S. Pat. No. 6,917,726, each of which is incorporated herein by reference in its entirety for all purposes. See also Levene et al. (2003) "Zero-mode waveguides for single-molecule analysis at high concentrations" Science 299:682-686 and U.S. Pat. Nos. 7,056,676, 7,056,661, 7,052,847, and 7,033,764, the full disclosures of which are incorporated herein by reference in their entirety for all purposes. Although various embodiments of the invention are described primarily in terms of zero-mode waveguide substrates, other types of substrates comprising appropriately configured reaction regions are known in the art and useful with the methods, compositions, and systems described herein, including but not limited to waveguide substrates, TIRF substrates, and the like. See, e.g., U.S. Patent Publication Nos. 20080128627 and 20100065726; and U.S. Ser. No. 61/192,326 (filed Sep. 16, 2009), and 61/306,235 (filed Feb. 19, 2010), all of which are incorporated herein by reference in their entireties for all purposes.

In certain embodiments, a surface-immobilized template localizing moiety fixes the template strand within, e.g., a ZMW, in the presence of one or more nucleotides and/or one or more nucleotide analogues, e.g., fluorescently labeled nucleotides or nucleotide analogs. For example, in certain embodiments, labeled analogues are present representing analogous compounds to each of the four natural nucleotides, A, T, G and C, e.g., in separate polymerase reactions, as in classical Sanger sequencing, or multiplexed together, e.g., in a single reaction, as in multiplexed sequencing approaches. When a particular base in the template strand is encountered by a polymerase during the polymerization reaction, it complexes with an available analogue that is complementary to such nucleotide, and incorporates that analogue into the nascent and growing nucleic acid strand. In one aspect, incorporation can result in a label being released, e.g., in polyphosphate analogues, cleaving between the $\alpha$ and $\beta$ phosphorus atoms in the analogue, and consequently releasing the labeling group (or a portion thereof). The incorporation event is detected, either by virtue of a longer presence of the analogue and, thus, the label, in the complex, or by virtue of release of the label group into the surrounding medium. Where different labeling groups are used for each of the types of analogues, e.g., A, T, G or C, identification of a label of an incorporated analogue allows identification of that analogue and consequently, determination of the complementary nucleotide in the template strand being processed at that time. Sequential reaction and monitoring permits a real-time monitoring of the polymerization reaction and determination of the sequence of the template nucleic acid. As noted elsewhere herein, embodiments comprising immobilized sequencing enzymes and, optionally, template nucleic acids that are not immobilized, are also contemplated.

As noted above, in particularly preferred aspects, the template localizing moiety, e.g., that is configured to interact with a polymerase, is provided immobilized within an optical confinement that permits observation of an individual template-dependent synthesis reaction in, e.g., a zero-mode waveguide. An immobilized template localizing moiety can fix a template to a surface, beneficially provide longer and more accurate sequence reads. For example, a polymerase that has sustained photodamage as a result of exposure to the optical energy of the fluorescently labeled nucleotides or nucleotide analogues present in the reaction mix can exchange with, e.g., a non-photodamaged polymerase, during a template-dependent polymerization reaction; or a first polymerase having a first error profile can be replaced with a second polymerase having a second error profile.

In addition to their use in sequencing, the surface-immobilized template localizing moieties of the invention are also useful in a variety of other analyses, e.g., real time monitoring of amplification, e.g., real-time-PCR methods, and the like. For example, real-time nucleic amplification reactions that include one or very few nucleic acid template molecules can be performed more efficiently if the template and polymerase were co-localized, e.g., by surface-immobilized template localizing moiety, e.g., that has been configured to interact with a polymerase. Further details regarding sequencing and nucleic acid amplification can be found, e.g., Berger and Kimmel, *Guide to Molecular Cloning Techniques, Methods in Enzymology volume* 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2001 ("Sambrook"); *Current Protocols in Molecular Biology*, F. M. Ausubel et al., eds., Current Protocols, a joint venture between Greene Publishing Associates, Inc. and John Wiley & Sons, Inc ("Ausubel"); Kaufman et al. (2003) Handbook of Molecular and Cellular Methods in Biology and Medicine Second Edition Ceske (ed) CRC Press (Kaufman); and *The Nucleic Acid Protocols Handbook* Ralph Rapley (ed) (2000) Cold Spring Harbor, Humana Press Inc (Rapley).

Further Details Regarding Integration of Methods/Compositions into High Throughput Sequencing Systems The methods and compositions provided by the invention can advantageously be integrated with systems that can, e.g., automate and/or multiplex the sequencing reactions comprising a surface-immobilized template localizing moiety. Systems of the invention can include one or more modules, e.g., that automate a method herein, e.g., for high-throughput sequencing applications. Such systems can include fluid-handling elements and controllers that move reaction components into contacts with one another, signal detectors, system software/instructions, e.g., to convert a sequence of fluorescent signals into nucleotide sequence information, and the like.

Systems provided by the invention include a reaction region in which a template localizing moiety and/or a sequencing enzyme has been immobilized, e.g., with a covalent bond. The template localizing moiety in the reaction region can optionally be configured to interact with a sequencing enzyme, e.g., any one of the sequencing enzymes described herein. The one or more single-molecule reaction region of the system can optionally include a sequencing enzyme, which, in certain embodiments of the systems, can be covalently linked to the surface-immobilized template localizing moiety, e.g., via a polymerase's C-terminal end (see FIG. 4) or linked, e.g., via a reversibly cleavable linker, e.g., a linker that can reform with a new sequencing enzyme.

In preferred embodiments, the sequencing enzyme can form a non-covalent complex with the template localizing moiety in the reaction region such that the sequencing enzyme can exchange with a second sequencing enzyme present, e.g., in a reaction mixture, without interrupting the sequencing reaction. This can beneficially provide longer and more accurate sequence reads. For example, a sequencing enzyme that has sustained photodamage as a result of exposure to the optical energy of the fluorescently labeled nucleotides or nucleotide analogues present in the reaction mix can exchange with, e.g., a non-photodamaged sequencing enzyme, during a sequencing reaction. Further, the exchange of sequencing enzymes having complementary characteristics, especially complementary error profiles, can facilitate generation of much richer sequencing data that can be analyzed to provide more accurate consensus sequence information than sequencing data from a single polymerase enzyme.

The reaction region can optionally comprise a planar surface, well, or one or more single-molecule reaction region. In preferred embodiments, the reaction region can optionally comprise one or more zero-mode waveguides (ZMWs). (See, e.g., Levene et al. (2003) "Zero-mode waveguides for single-molecule analysis at high concentrations" Science 299:682-686 and U.S. Pat. Nos. 7,056,676, 7,056, 661, 7,052,847, and 7,033,764, the full disclosures of which are incorporated herein by reference in their entirety for all purposes.)

Systems of the invention can optionally include modules that provide for detection or tracking of products, e.g., a fluorescent light from one or more fluorophore that is linked to a nucleotide or nucleotide analog that is being incorporated into a growing nucleic acid. Detectors can include spectrophotometers, epifluorescent detectors, CCD arrays, CMOS arrays, microscopes, cameras, or the like. Optical labeling is particularly useful because of the sensitivity and ease of detection of these labels, as well as their relative handling safety, and the ease of integration with available detection systems (e.g., using microscopes, cameras, photomultipliers, CCD arrays, CMOS arrays and/or combinations thereof). High-throughput analysis systems using optical labels include DNA sequencers, array readout systems, cell analysis and sorting systems, and the like. For a brief overview of fluorescent products and technologies see, e.g., Sullivan (ed) (2007) *Fluorescent Proteins*, Volume 85, Second Edition (Methods in Cell Biology) (Methods in Cell Biology) ISBN-10: 0123725585; Hof et al. (eds) (2005) *Fluorescence Spectroscopy in Biology: Advanced Methods and their Applications to Membranes, Proteins, DNA, and Cells* (Springer Series on Fluorescence) ISBN-10: 354022338X; Haughland (2005) *Handbook of Fluorescent Probes and Research Products*, 10th Edition (Invitrogen, Inc./Molecular Probes); *BioProbes Handbook*, (2002) from Molecular Probes, Inc.; and Valeur (2001) *Molecular Fluorescence: Principles and Applications* Wiley ISBN-10: 352729919X. System software, e.g., instructions running on a computer can be used to track and inventory reactants or products, and/or for controlling robotics/fluid handlers to achieve transfer between system stations/modules. The overall system can optionally be integrated into a single apparatus, or can consist of multiple apparatus with overall system software/instructions providing an operable linkage between modules.

The systems of the invention also typically include information processors or computers operably coupled to the detection portions of the systems, in order to store the signal data obtained from the detector(s) on a computer readable medium, e.g., hard disk, CD, DVD or other optical medium, flash memory device, or the like. For purposes of this aspect of the invention, such operable connection provide for the electronic transfer of data from the detection system to the processor for subsequent analysis and conversion. Operable connections may be accomplished through any of a variety of well-known computer networking or connecting methods, e.g., Firewire®, USB connections, wireless connections, WAN or LAN connections, or other connections that preferably include high data transfer rates.

The computers typically include data processing systems (e.g., software and algorithm implementations) that analyze the raw signal data, identify signal pulses that are likely associated with incorporation events, and identify bases incorporated during the sequencing reaction, in order to convert or transform the raw signal data into user interpretable sequence data, and for transforming sequence read data into consensus sequence data. In certain preferred embodiments, sequence read data is determined from data generated using a sequencing-by-synthesis technology, as described elsewhere herein, other sequencing technologies known to those of ordinary skill in the art may also be used, e.g., pyrosequencing, ligation-mediated sequencing, Sanger sequencing, capillary electrophoretic sequencing, etc. Further, the data processing systems can include software and algorithm implementations configured to transform redundant sequence read data into consensus sequence data, which is generally more representative of the actual sequence of a template nucleic acid molecule than sequence read data from a single read of a single template nucleic acid molecule. The transformation of the sequence read data (e.g., redundant sequence read data) into consensus sequence data identifies and negates some or all of the single-read variation between the multiple reads in the redundant sequence read data. As such, the transformation provides a representation of the actual nucleotide sequence of the nucleic acid template from which redundant sequence read data is generated that is more accurate than a representation based on a single read. Further, in embodiments in which multiple different types polymerases are used, the representation of the actual nucleotide sequence of the nucleic acid template from which redundant sequence read data is generated that is more accurate than a representation based on one or more reads from a single polymerase. Such machines and methods for using them are available to the ordinary practioner. Exemplary systems and software are described in detail in, e.g., Published U.S. Patent Application Nos. 2009-0024331, 2010-0169026, 2010-0075327, and 2008-0277595, and U.S. Provisional Application Nos. 61/307,672 and 61/307,732, filed Feb. 24, 2010, the full disclosures of which are incorporated herein by reference in their entireties for all purposes.

The software and algorithm implementations are preferably machine-implemented methods, e.g., carried out on a machine comprising computer-readable medium configured to carry out various aspects of the methods herein. For example, the computer-readable medium preferably comprises at least one or more of the following: a) a user interface; b) memory for storing sequence read data; c) memory storing software-implemented instructions for carrying out the algorithms for transforming redundant sequence read data into consensus sequence data; d) a processor for executing the instructions; e) software for recording the results of the transformation into memory; and f) memory for recordation and storage of the resulting consensus sequence read data. In preferred embodiments, the user interface is used by the practitioner to manage various aspects of the machine, e.g., to direct the machine to carry out the various steps in the transformation of redundant sequence read data into consensus sequence data, recordation of the results of the transformation, and management of the consensus sequence data stored in memory.

As such, in preferred embodiments, the methods further comprise a transformation of the computer-readable medium by recordation of the sequence read data and/or the consensus sequence data generated by the methods. Further, the computer-readable medium may comprise software for providing a graphical representation of the sequence read data and/or the consensus sequence read data, and the graphical representation may be provided, e.g., in soft-copy (e.g., on an electronic display) and/or hard-copy (e.g., on a print-out) form. Such data processing systems typically comprise a computer processor for processing the sequence read data and computer usable medium for storage of the initial sequence read data and/or the results of one or more steps of the transformation (e.g., the consensus sequence data), such as the computer-readable medium described above.

In certain embodiments multiple types of polymerases are used to process a single template or multiple copies of identical templates, as described above. Algorithms for determination of polymerase identity are used to identify the type of polymerase processing a template and/or that produced a given sequence read. In certain embodiments, information is collected about the sequencing characteristics of each type of polymerase enzyme in use. This information can include intrinsic pulse characteristics, such as pulse duration, inter-pulse duration, characteristic pulse intensity, emission spectra (e.g., spectral shape, wavelength, and the like), response to template sequence context, etc.; extrinsic pulse characteristics, including the template strand local sequence context up to or exceeding the extent of the DNA or RNA molecule interacting with the polymerase, template strand global sequence context, template secondary structure, the concentration and identity of nucleotide analogs and other chemicals in the sequencing mix at the time of the pulse; and error characteristics, such as the rate or frequency of incorporations without a visible or recorded pulse, non-cognate extra pulses, cognate extra pulses, branch pulses, initiation and termination contexts, and other error modes. All such information is collected on a per-pulse basis, and joint distributions of some or all of the parameters above are estimated. These distributions are used to construct probability models of pulse streams associated with each type of polymerase enzyme in use.

A pulse stream of nucleotide incorporation event pulses generated during a sequencing reaction is scanned to map blocks of pulses likely to be emitted by a single polymerase or a single type of polymerase. The boundaries between such blocks may be pauses in the pulse stream, regions of low quality pulses as determined by their abnormal or inconsistent pulse characteristics, or regions with multiple pulses detected in the same frame, indicative of the presence of more than one polymerase in the sequencing volume.

In preferred embodiments, algorithms for determination of pulse identity use information about the sequencing characteristics and error profiles of each type of polymerase in use to determine the identity of the polymerase and estimate the template sequence simultaneously at each position in the pulse stream, given information from the pulse stream and relevant information extrinsic to the pulse stream. This determination is typically performed using an appropriate machine learning algorithm, such as a hidden Markov model, conditional random field, support vector machine, or other algorithm capable of training on the per-polymerase data collected as described above, and capable of estimating the polymerase identity and the template sequence according to the model associated with that polymerase identity simultaneously. This estimation can be performed separately for each block delimited as described above, or simultaneously with the estimation of such blocks, using a probabilistic model capable of estimating transitions between polymerase identities, e.g. a hidden Markov model incorporating such transitions. The estimation of polymerase identity can be affected by knowledge of relative concentrations of the polymerases in the sequencing mix.

In certain embodiments, algorithms for identifying a polymerase based upon sequence data involve collecting the 3-base pulse duration data and making a table with $4^3$ entries representing the average pulse widths for all of the possible sequence contexts. This table is analyzed by methods known in the art (e.g., dot product, chi-squared, SVM, CART, boosted CART, etc.) to decide which of the several reference tables looks most like the sequence data in question. A similar approach can be used with respect to any data compilation from the pulse statistics.

Alternatively, if the identity of the type of polymerase is known at each time point in the pulse stream, then the pulse stream is estimated from the model associated with the polymerase known to be present without estimating the identity of the polymerase. For example, one polymerase can be removed from the reaction mixture and a different polymerase type can be added at a known point in time (e.g., by buffer exchange). Alternatively, different types of polymerases can be immobilized at known locations, e.g., on an array, such that signal data emanating from each location can be attributed to a single type of polymerase. In further embodiments, each different type of polymerase is linked to a distinct label, the detection of which identifies the polymerase type, e.g., all polymerase As are linked to label A, all polymerase B's are linked to label B, and label A and label B are optically distinguishable from one another at a reaction region.

Once the polymerase has been identified, an optimal base-calling algorithm can be selected that takes into consideration the particular characteristics (e.g., pulse and error characteristics) of that polymerase under a given set of reaction conditions. Such algorithms are used to combine the sequencing data from multiple different polymerases acting on a single template or on multiple individual copies of the same template, e.g., at optically resolvable locations on a substrate or array. In certain embodiments, the estimated template sequence is decorated with quality values, which reflect the confidence in the estimate of each nucleotide's identity. These quality values reflect the consistency of pulse characteristics for the nucleotide with those characteristics expected by the probabilistic model described above, as well as the known intrinsic sequencing characteristics (e.g., fidelity, rate, etc.) of the active polymerase, e.g., relative to other polymerases in use. A detailed discussion of base-calling operations and considerations is found in, e.g., U.S. Patent Publication No. 20090024331 and U.S. Ser. No. 61/307,672, filed Feb. 24, 2010, the disclosures of which are incorporated herein by reference in their entireties for all purposes.

In certain embodiments, redundant sequence information is analyzed by aligning the sequences from different individual sequence reads to each other and, if available, to an extrinsic reference sequence. Redundant sequence information can be generated in various ways, e.g., by repeatedly sequencing a circular or SMRTbell™ template (see, e.g., U.S. Patent Publication No. 20090298075, incorporated herein by reference in its entirety for all purposes), by resequencing a single template under various different reaction conditions (e.g., having different pH, temperature, polymerase content, divalent cation concentration, illumination frequency, power, intensity, and/or wavelength, etc.), or by sequencing identical templates to generate a set of reads, each corresponding to a single one of the identical templates. For example, the same polymerase can be used to repeatedly sequence the same template under different conditions, e.g., conditions that promote fidelity versus conditions that promote processivity, and the set of sequence reads generated will comprise redundant sequence information. The set of sequence reads is aligned, optionally including the reference sequence, and a consensus algorithm is used to estimate the template sequence with higher accuracy from this multiple sequence alignment. Quality values, assigned as described above according to probability models associated with each polymerase, affect the weight that their associated nucleotide identity estimates carry relative to other estimates in the same column of the multiple sequence alignment. The resulting estimate of each nucleotide in the template sequence is computed using a Bayesian classifier or another appropriate probabilistic model. This configuration of a consensus base-calling algorithm ("base caller") is well known in the art. In certain embodiments, an algorithm is used that constructs a maximum likelihood algorithm that uses the polymerase identity in each read as a prior, and then evaluates the most likely genome sequence given the reads from the two types of sequencing conditions. Base-calling and consensus determination algorithms and methods well known in the art are applicable to the sequencing methods described herein, including, e.g., Published U.S. Patent Application Nos. 2009-0024331, 2010-0169026, 2010-0075327, and 2008-0277595, and U.S. Provisional Application Nos. 61/307,672 and 61/307,732, filed Feb. 24, 2010, the full disclosures of which are incorporated herein by reference in their entireties for all purposes.

Kits

The present invention also provides kits that incorporate the compositions of the invention. Such kits can include, e.g., a template localizing moiety packaged in a fashion to permit its covalent binding to a surface of interest. Alternatively surface-bound template localizing moieties can be provided as components of the kits, or the surface can be provided with binding partners suitable to bind the template localizing moieties, which are optionally packaged separately. Instructions for making or using surface-bound template localizing moieties are an optional feature of the invention. In related embodiments, such kits can include a sequencing enzyme packaged in a fashion to permit its covalent binding to a surface of interest. Alternatively surface-bound sequencing enzyme can be provided as components of the kits, or the surface can be provided with binding partners suitable to bind the sequencing enzymes, which are optionally packaged separately. Instructions for making or using surface-bound sequencing enzymes are an optional feature of the invention. Further, the kits can include a combination of template localizing moieties and sequencing enzyme, either or both of which are (or are to be) covalently or non-covalently attached to a surface of interest.

The template localizing moieties provided in such kits can also comprise polynucleotide complementary to a polynucleotide sequence of interest in a template nucleic acid to facilitate selective immobilization of a subset of template nucleic acids having one or more particular polynucleotide sequences of interest (e.g., exonic or intronic regions, regulatory regions, and the like). For example, a kit can comprise a pool of template localizing moieties having polynucleotide regions complementary to a set of genetic loci known to predict susceptibility to a given disease, identify an unknown microorganism, determine paternity, and other forensic, medical, and agricultural analyses. Only genomic fragments having one or more of those genetic loci of interest will be targeted and immobilized by the template localizing moieties, and subsequently subjected to sequence analysis, thereby allowing selective analysis of a subset of a complex genomic sample and a reduction in the complexity of the data set so generated.

Such kits can also optionally include additional useful reagents such as one or more nucleotide analogs, e.g., for sequencing, nucleic acid amplification, or the like. For example, the kits can include one or more sequencing enzymes, e.g., packaged in such a manner as to enable their use with a template localizing moiety, a set of different nucleotide analogs of the invention, e.g., those that are analogous to A, T, G, and C, e.g., where one or more of the analogs comprise a detectable moiety, to permit identification in the presence of the analogs. The kits of the invention can optionally include natural nucleotides, a control template, and other reagents, such as buffer solutions and/or salt solutions, including, e.g., divalent metal ions, i.e., $Mg^{++}$, $Mn^{++}$ and/or $Fe^{++}$, standard solutions, e.g., dye standards for detector calibration, etc. Such kits also typically include instructions for use of the compounds and other reagents in accordance with the desired application methods, e.g., nucleic acid sequencing, nucleic acid labeling, amplification, enzymatic detection systems, and the like.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference in their entireties for all purposes.

What is claimed is:

1. A method of sequencing a single template molecule, the method comprising:
   localizing the single template molecule to a reaction region through association with a template localizing moiety attached to the reaction region, wherein the template localizing moiety comprises a protein that translocates along the single template molecule and does not synthesize a polynucleotide complementary to the single template molecule while retaining the single template molecule at the reaction region; and
   sequencing a polynucleotide region of the localized single template molecule to obtain a first polynucleotide sequence read of the polynucleotide region, wherein the polynucleotide sequence read comprises redundant sequence information for the polynucleotide region, thereby sequencing the single template molecule.

2. The method of claim 1, wherein a single strand of the single template nucleic acid can move through the template localizing moiety.

3. The method of claim 1, wherein the template localizing moiety topologically encircles the single template molecule.

4. The method of claim 1, wherein the protein is selected from the group consisting of: a helicase, a sliding clamp, a DNA repair enzyme, and a polymerase mutant, fragment, or subunit thereof that does not synthesize a polynucleotide complementary to the single template molecule.

5. The method of claim 1, wherein the template localizing moiety catalyzes unidirectional, processive strand separation on the single template molecule.

6. The method of claim 1, wherein the reaction region comprises a zero-mode waveguide.

7. The method of claim 1, wherein the single template molecule is a circular template molecule.

8. The method of claim 1, wherein the single template molecule comprises a double-stranded fragment and an end annealed to a stem-loop adapter.

9. The method of claim 1, wherein the sequencing comprises a method selected from the group consisting of exonuclease sequencing, nanopore-based sequencing, and sequencing by synthesis.

10. The method of claim 1, wherein the sequencing comprises monitoring the reaction region in real time.

11. A method of sequencing a single nucleic acid molecule, the method comprising:
   localizing the single nucleic acid molecule to a reaction region through association with a template localizing moiety attached to the reaction region, wherein the template localizing moiety comprises a protein selected from the group consisting of: a helicase, a sliding clamp, a DNA repair enzyme, and a polymerase mutant, fragment, or subunit thereof that does not synthesize a polynucleotide complementary to the single template molecule; and sequencing a polynucleotide region of the localized single template nucleic acid molecule using a method selected from the group consisting of exonuclease sequencing, nanopore-based sequencing, and sequencing by synthesis to obtain a polynucleotide sequence read of the polynucleotide region, thereby sequencing the single nucleic acid molecule.

12. The method of claim 11, wherein the reaction region comprises a zero-mode waveguide.

13. The method of claim 11, wherein the single nucleic acid molecule is a circular template molecule.

14. The method of claim 11, wherein the single nucleic acid molecule comprises a double-stranded fragment comprising at least one stem-loop adapter annealed to an end.

15. The method of claim 11, wherein the sequencing comprises monitoring the reaction region in real time.

16. A method of generating redundant sequence information for a polynucleotide region from multiple template nucleic acid molecules, the method comprising:

providing multiple template nucleic acid molecules, each of which comprises the same polynucleotide region;

localizing each of the template nucleic acid molecules to a different reaction region through association with a template localizing moiety attached to each reaction region, wherein each template localizing moiety encircles each template nucleic acid molecule such that a strand of said template nucleic acid molecule can move through the template localizing moiety, and further wherein the template localizing moiety does not synthesize a polynucleotide complementary to the single template molecule;

sequencing the polynucleotide region in each of the template nucleic acid molecules using a method selected from the group consisting of: exonuclease sequencing, nanopore-based sequencing, and sequencing by synthesis to obtain multiple polynucleotide sequence reads of the polynucleotide region, wherein the polynucleotide sequence reads comprises redundant sequence information for the polynucleotide region, thereby generating redundant sequence information from the template nucleic acid molecules.

17. The method of claim 16, wherein each template localizing moiety comprises a protein lacking nascent strand synthesis activity that translocates along the template nucleic acid molecules while retaining the template nucleic acid molecules at each different reaction region.

18. The method of claim 16, wherein each template localizing moiety comprises a protein selected from the group consisting of: a helicase, a sliding clamp, a DNA repair enzyme, and a polymerase mutant, fragment, or subunit thereof that does not synthesize a polynucleotide complementary to the single template molecule.

19. The method of claim 16, wherein each template localizing moiety catalyzes unidirectional, processive strand separation on each single template molecule.

20. The method of claim 16, wherein each reaction region comprises a zero-mode waveguide.

21. The method of claim 16, wherein the sequencing comprises monitoring each of the different reaction regions in real time.

* * * * *